US012097265B2

(12) United States Patent
Gong et al.

(10) Patent No.: US 12,097,265 B2
(45) **Date of Patent: *Sep. 24, 2024**

(54) CYTOTOXIC PARTICLES FOR TARGETING P2X7 RECEPTOR

(71) Applicant: BIOSCEPTRE (AUST) PTY LTD, North Ryde (AU)

(72) Inventors: Xiaojuan Gong, New South Wales (AU); Minoo J Moghaddam, New South Wales (AU); Julian Alexander Barden, New South Wales (AU)

(73) Assignee: BIOSCEPTRE (AUST) PTY LTD, North Ryde (AU)

( * ) Notice: Subject to any disclaimer, the term of this patent is extended or adjusted under 35 U.S.C. 154(b) by 288 days.

This patent is subject to a terminal disclaimer.

(21) Appl. No.: 17/575,568

(22) Filed: Jan. 13, 2022

(65) Prior Publication Data

US 2022/0249692 A1 Aug. 11, 2022

Related U.S. Application Data

(63) Continuation of application No. 16/326,882, filed as application No. PCT/AU2017/050885 on Aug. 18, 2017, now Pat. No. 11,260,131.

(30) Foreign Application Priority Data

Oct. 21, 2016 (AU) ................................ 2016904292

(51) Int. Cl.
| | |
|---|---|
| *A61K 47/69* | (2017.01) |
| *A61K 9/127* | (2006.01) |
| *A61K 9/16* | (2006.01) |
| *A61K 31/7068* | (2006.01) |
| *A61K 47/54* | (2017.01) |
| *A61K 47/68* | (2017.01) |
| *A61P 35/00* | (2006.01) |
| *C07K 16/18* | (2006.01) |
| *C07K 16/28* | (2006.01) |
| *C07K 16/30* | (2006.01) |
| *A61K 39/00* | (2006.01) |

(52) U.S. Cl.
CPC .......... *A61K 47/6913* (2017.08); *A61K 9/127* (2013.01); *A61K 9/1271* (2013.01); *A61K 9/1617* (2013.01); *A61K 31/7068* (2013.01); *A61K 47/542* (2017.08); *A61K 47/545* (2017.08); *A61K 47/6849* (2017.08); *A61P 35/00* (2018.01); *C07K 16/18* (2013.01); *C07K 16/28* (2013.01); *C07K 16/30* (2013.01); *A61K 2039/505* (2013.01); *A61K 2039/545* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 7,183,064 B1 | 2/2007 | Slater et al. | |
| 7,326,415 B2 | 2/2008 | Barden et al. | |
| 7,531,171 B2 | 5/2009 | Barden et al. | |
| 7,888,473 B2 | 2/2011 | Barden et al. | |
| 8,067,550 B2 | 11/2011 | Barden et al. | |
| 8,080,635 B2 | 12/2011 | Barden et al. | |
| 8,293,491 B2 | 10/2012 | Gidley-Baird et al. | |
| 8,399,617 B2 | 3/2013 | Barden et al. | |
| 8,440,186 B2 | 5/2013 | Barden et al. | |
| 8,597,643 B2 | 12/2013 | Barden et al. | |
| 8,658,385 B2 | 2/2014 | Gidley-Baird et al. | |
| 8,709,425 B2 | 4/2014 | Barden et al. | |
| 8,835,609 B2 | 9/2014 | Barden et al. | |
| 9,127,059 B2 | 9/2015 | Barden et al. | |
| 9,181,320 B2 | 11/2015 | Barden et al. | |
| 9,328,155 B2 | 5/2016 | Barden et al. | |
| 9,428,587 B2 | 8/2016 | Barden et al. | |
| 9,562,094 B2 | 2/2017 | Barden et al. | |
| 9,566,318 B2 | 2/2017 | Barden et al. | |
| 9,663,584 B2 | 5/2017 | Barden et al. | |
| 9,688,771 B2 | 6/2017 | Barden et al. | |
| 10,053,508 B2 | 8/2018 | Barden et al. | |
| 10,232,025 B2 | 3/2019 | Barden et al. | |
| 10,238,716 B2 | 3/2019 | Barden et al. | |
| 10,245,308 B2 | 4/2019 | Barden et al. | |
| 2004/0067196 A1 * | 4/2004 | Brunke ............. | A61K 51/1045 424/1.49 |
| 2004/0067542 A1 | 4/2004 | Barden et al. | |
| 2004/0067967 A1 | 4/2004 | Barden et al. | |

(Continued)

FOREIGN PATENT DOCUMENTS

| | | |
|---|---|---|
| AU | 2002322192 B2 | 5/2008 |
| WO | WO 01/06259 A1 | 1/2001 |
| WO | WO 02/057306 A1 | 7/2002 |
| WO | WO 03/020762 A1 | 3/2003 |
| WO | WO 2008/043145 A1 | 4/2008 |
| WO | WO 2008/043146 A1 | 4/2008 |
| WO | WO 2009/033233 A1 | 3/2009 |
| WO | WO 2009/033234 A1 | 3/2009 |
| WO | WO 2010/000041 A1 | 1/2010 |
| WO | WO 2011/020155 A1 | 2/2011 |

(Continued)

OTHER PUBLICATIONS

Cheng et al., "The use of single chain Fv as targeting agents for immunoliposomes: an update on immunoliposomal drugs for cancer treatment", Expert Opinion on Drug Delivery, 2010, 7(4): 461-478.

(Continued)

*Primary Examiner* — Laura B Goddard
(74) *Attorney, Agent, or Firm* — James S. Keddie; Bozicevic, Field & Francis LLP

(57) ABSTRACT

The invention relates to cytotoxic particles for cancer therapy including a core and a plurality of variable domains arranged on the core for binding to P2X7 receptors on a cancer cell.

19 Claims, 14 Drawing Sheets

Specification includes a Sequence Listing.

(56) References Cited

U.S. PATENT DOCUMENTS

| | | | |
|---|---|---|---|
| 2007/0248963 | A1 | 10/2007 | Slater et al. |
| 2008/0227122 | A1 | 9/2008 | Barden et al. |
| 2010/0036101 | A1 | 2/2010 | Gidley-Baird et al. |
| 2011/0111431 | A1 | 5/2011 | Slater et al. |
| 2012/0282278 | A1* | 11/2012 | Barden .................. A61P 35/00 536/23.53 |
| 2014/0323693 | A1 | 10/2014 | Barden et al. |
| 2017/0327592 | A1 | 11/2017 | Barden et al. |
| 2018/0037650 | A1 | 2/2018 | Barden |

FOREIGN PATENT DOCUMENTS

| | | | |
|---|---|---|---|
| WO | WO 2011/075789 | A1 | 6/2011 |
| WO | WO 2012/031333 | A1 | 3/2012 |
| WO | WO 2013/003895 | A1 | 1/2013 |
| WO | WO 2016/154683 | A1 | 10/2016 |

OTHER PUBLICATIONS

Kontermann, "Immunoliposomes for cancer therapy", Current Opinion in Molecular Therapeutics, 2006, 8(1): 39-45.

Steeland et al., "Nanobodies as therapeutics: big opportunities for small antibodies", Drug Discovery Today, 2016, 21(7): 1076-1113.

Federico et al., "Gemcitabine-loaded liposomes: rationale, potentialities and future perspectives", International Journal of Nanomedicine, 2012, 7: 5423-5436.

Shin et al., "CD133 antibody-conjugated immunoliposomes encapsulating gemcitabine for targeting glioblastoma stem cells", Journal of Materials Chemistry B, 2014, 2: 3771-3781.

Crystal Research Associates: "Biosceptre—Executive Informational Overview", Jul. 26, 2016, retrieved from the Internet: URL:http://www.baystreet.ca/articles/research_reports/crystal/BIOSCEPTRE_Executive_Informational_Overview_07-26-16.pdf [retrieved on May 6, 2020].

Gilbert et al., "ATP in the tumour microenvironment drives expression of nfP2X7, a key mediator of cancer cell survival", Oncogene, 2018, 38(2):194-208.

Supplemental European Search Report issued for European Application No. 17862514.1, May 26, 2020.

Immordino et al., "Preparation, characterization, cytotoxicity and pharmacokinetics of liposomes containing lipophilic gemcitabine prodrugs", Journal of Controlled Release, 2004, 100: 331-346.

Guo, General Introduction to Medicinal Chemistry, 2nd Edition, China Medical Science Press, Aug. 2003, p. 507.

Barden et al., "Non-Functional P2X7: A Novel and Ubiquitous Target in Human Cancer", Journal of Clinical & Cellular Immunology, 2014, 5:4, 5 pages.

Gong et al., "Lamellar crystalline self-assembly behaviour and solid lipid nanoparticles of a palmityl prodrug analogue of Capecitabine—A chemotherapy agent", Colloids and Surfaces B: Biointerfaces, 2011, 85: 349-359.

Mura et al., "Lipid prodrug nanocarriers in cancer therapy", Journal of Controlled Release, 2015, 208: 25-41.

Shin et al., "Herceptin-conjugated temperature-sensitive immunoliposomes encapsulating gemcitabine for breast cancer", Archives of Pharmacal Research, 2016, 39: 350-358.

* cited by examiner

1. Ladder
2. BIL03s Ab standard
3. Activated BIL03s
4. BIL03s coated NPs showed protein conjugation
5. Antibody isotype control HEL4 Standard
6. HEL4 coated NPs

SEQUENCE LISTING

<160> NUMBER OF SEQ ID NOS: 8

<210> SEQ ID NO 1
<211> LENGTH: 595
<212> TYPE: PRT
<213> ORGANISM: Homo sapiens

<400> SEQUENCE: 1

```
Met Pro Ala Cys Cys Ser Cys Ser Asp Val Phe Gln Tyr Glu Thr Asn
1               5                   10                  15

Lys Val Thr Arg Ile Gln Ser Met Asn Tyr Gly Thr Ile Lys Trp Phe
            20                  25                  30

Phe His Val Ile Ile Phe Ser Tyr Val Cys Phe Ala Leu Val Ser Asp
        35                  40                  45

Lys Leu Tyr Gln Arg Lys Glu Pro Val Ile Ser Ser Val His Thr Lys
    50                  55                  60

Val Lys Gly Ile Ala Glu Val Lys Glu Glu Ile Val Glu Asn Gly Val
65                  70                  75                  80

Lys Lys Leu Val His Ser Val Phe Asp Thr Ala Asp Tyr Thr Phe Pro
                85                  90                  95

Leu Gln Gly Asn Ser Phe Phe Val Met Thr Asn Phe Leu Lys Thr Glu
            100                 105                 110

Gly Gln Glu Gln Arg Leu Cys Pro Glu Tyr Pro Thr Arg Arg Thr Leu
        115                 120                 125

Cys Ser Ser Asp Arg Gly Cys Lys Lys Gly Trp Met Asp Pro Gln Ser
    130                 135                 140

Lys Gly Ile Gln Thr Gly Arg Cys Val Val His Glu Gly Asn Gln Lys
145                 150                 155                 160

Thr Cys Glu Val Ser Ala Trp Cys Pro Ile Glu Ala Val Glu Glu Ala
                165                 170                 175

Pro Arg Pro Ala Leu Leu Asn Ser Ala Glu Asn Phe Thr Val Leu Ile
            180                 185                 190

Lys Asn Asn Ile Asp Phe Pro Gly His Asn Tyr Thr Thr Arg Asn Ile
        195                 200                 205

Leu Pro Gly Leu Asn Ile Thr Cys Thr Phe His Lys Thr Gln Asn Pro
    210                 215                 220

Gln Cys Pro Ile Phe Arg Leu Gly Asp Ile Phe Arg Glu Thr Gly Asp
225                 230                 235                 240

Asn Phe Ser Asp Val Ala Ile Gln Gly Gly Ile Met Gly Ile Glu Ile
                245                 250                 255

Tyr Trp Asp Cys Asn Leu Asp Arg Trp Phe His His Cys Arg Pro Lys
            260                 265                 270

Tyr Ser Phe Arg Arg Leu Asp Asp Lys Thr Thr Asn Val Ser Leu Tyr
        275                 280                 285

Pro Gly Tyr Asn Phe Arg Tyr Ala Lys Tyr Tyr Lys Glu Asn Asn Val
    290                 295                 300

Glu Lys Arg Thr Leu Ile Lys Val Phe Gly Ile Arg Phe Asp Ile Leu
305                 310                 315                 320

Val Phe Gly Thr Gly Gly Lys Phe Asp Ile Ile Gln Leu Val Val Tyr
```

```
                        325                 330                 335
    Ile Gly Ser Thr Leu Ser Tyr Phe Gly Leu Ala Ala Val Phe Ile Asp
                    340                 345                 350

Phe Leu Ile Asp Thr Tyr Ser Ser Asn Cys Cys Arg Ser His Ile Tyr
                355                 360                 365

Pro Trp Cys Lys Cys Cys Gln Pro Cys Val Val Asn Glu Tyr Tyr
        370                 375                 380

Arg Lys Lys Cys Glu Ser Ile Val Glu Pro Lys Pro Thr Leu Lys Tyr
    385                 390                 395                 400

Val Ser Phe Val Asp Glu Ser His Ile Arg Met Val Asn Gln Gln Leu
                    405                 410                 415

Leu Gly Arg Ser Leu Gln Asp Val Lys Gly Gln Glu Val Pro Arg Pro
                420                 425                 430

Ala Met Asp Phe Thr Asp Leu Ser Arg Leu Pro Leu Ala Leu His Asp
                435                 440                 445

Thr Pro Pro Ile Pro Gly Gln Pro Glu Glu Ile Gln Leu Leu Arg Lys
            450                 455                 460

Glu Ala Thr Pro Arg Ser Arg Asp Ser Pro Val Trp Cys Gln Cys Gly
    465                 470                 475                 480

Ser Cys Leu Pro Ser Gln Leu Pro Glu Gly Ser His Arg Cys Leu Glu Glu
                    485                 490                 495

Leu Cys Cys Arg Lys Lys Pro Gly Ala Cys Ile Thr Thr Ser Glu Leu
                500                 505                 510

Phe Arg Lys Leu Val Leu Ser Arg His Val Leu Gln Phe Leu Leu Leu
            515                 520                 525

Tyr Gln Glu Pro Leu Leu Ala Leu Asp Val Asp Ser Thr Asn Ser Arg
    530                 535                 540

Leu Arg His Cys Ala Tyr Arg Cys Tyr Ala Thr Trp Arg Phe Gly Ser
    545                 550                 555                 560

Gln Asp Met Ala Asp Phe Ala Ile Leu Pro Ser Cys Cys Arg Trp Arg
                    565                 570                 575

Ile Arg Lys Glu Phe Pro Lys Ser Glu Gly Gln Tyr Ser Gly Phe Lys
                580                 585                 590

Ser Pro Tyr
            595

<210> SEQ ID NO 2
<211> LENGTH: 16
<212> TYPE: PRT
<213> ORGANISM: Homo sapiens

<400> SEQUENCE: 2

Gly His Asn Tyr Thr Thr Asn Ile Leu Pro Gly Leu Asn Ile Thr Cys
1               5                   10                  15

<210> SEQ ID NO 3
<211> LENGTH: 15
<212> TYPE: PRT
<213> ORGANISM: Homo sapiens

<400> SEQUENCE: 3

Lys Tyr Tyr Lys Glu Asn Asn Val Glu Lys Arg Thr Leu Ile Lys
1               5                   10                  15

<210> SEQ ID NO 4
<211> LENGTH: 6
<212> TYPE: PRT
```

-continued

```
<213> ORGANISM: Homo sapiens

<400> SEQUENCE: 4

Arg Asn His Asp Met Gly
1               5

<210> SEQ ID NO 5
<211> LENGTH: 17
<212> TYPE: PRT
<213> ORGANISM: Homo sapiens

<400> SEQUENCE: 5

Ala Ile Ser Gly Ser Gly Gly Ser Thr Tyr Tyr Ala Asn Ser Val Lys
1               5                   10                  15

Gly

<210> SEQ ID NO 6
<211> LENGTH: 11
<212> TYPE: PRT
<213> ORGANISM: Homo sapiens

<400> SEQUENCE: 6

Glu Pro Lys Pro Met Asp Thr Glu Phe Asp Tyr
1               5                   10

<210> SEQ ID NO 7
<211> LENGTH: 119
<212> TYPE: PRT
<213> ORGANISM: Homo sapiens

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asn His
                20                  25                  30

Asp Met Gly Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asn Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Glu Pro Lys Pro Met Asp Thr Glu Phe Asp Tyr Arg Ser Pro Gly
            100                 105                 110

Thr Leu Val Thr Val Ser Ser
        115

<210> SEQ ID NO 8
<211> LENGTH: 119
<212> TYPE: PRT
<213> ORGANISM: Homo sapiens

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asn His
                20                  25                  30

Asp Met Gly Trp Val Arg Gln Ala Pro Gly Lys Gly Leu Glu Trp Val
            35                  40                  45
```

```
Ser Ala Ile Ser Gly Ser Gly Gly Ser Thr Tyr Tyr Ala Asp Ser Val
    50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
                85              90              95

Ala Glu Pro Lys Pro Met Asp Thr Glu Phe Asp Tyr Arg Ser Pro Gly
            100             105             110

Thr Leu Val Thr Val Ser Ser
            115
```

CYTOTOXIC PARTICLES FOR TARGETING P2X7 RECEPTOR

CROSS-REFERENCE TO RELATED APPLICATION

This application is a continuation of U.S. application Ser. No. 16/326,882, filed on Feb. 20, 2019, which is a § 371 national phase of International Application No. PCT/AU2017/050885, filed on Aug. 18, 2017, which claims priority from Australian application AU 2016904292, filed on Oct. 21, 2016, the entire contents of which applications are herein incorporated by reference in their entirety.

FIELD OF THE INVENTION

The invention relates to chemotherapy of cancer, to formation of nanoparticles, especially liposomes, and to conjugation of cytotoxic drugs and antibodies to same.

BACKGROUND OF THE INVENTION

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

Most cancers are frequently treated by a combination of approaches, including surgical removal of a tumour, chemotherapy, and/or radiation therapy. Surgical procedures are usually not sufficient to remove a tumour in its entirety, so surgery is frequently accompanied by chemotherapy and/or radiation therapy. Chemotherapy involves the use of drugs to kill tumour cells, and radiation therapy involves treatment with high-energy rays (e.g. x-rays) to kill or shrink tumour cells.

Unfortunately, chemotherapy and radiation cause serious and sometimes life-threatening side effects, including fatigue; nausea; vomiting; pain; hair loss; anemia; central nervous system problems; infection; blood clotting problems; mouth, gum, and throat problems; diarrhea; constipation; nerve and muscle effects; kidney and bladder effects; flu-like symptoms; fluid retention; and effects on sexual organs.

Chemotherapy causes such severe side effects because the treatment involves the systemic administration of cytotoxic agents to a patient. These agents cannot distinguish tumour cells from normal cells and, therefore, kill healthy cells as well as tumour cells. Side effects are worsened because a very large dose must be administered to the patient in order to deliver a therapeutically effective dose to a tumour site. Although radiation therapy is administered somewhat more locally than chemotherapy, radiation treatment still results in the destruction of normal tissue in the vicinity of the tumour.

Thus, targeting of a therapeutic agent (e.g., to a particular tissue or cell type; to a specific diseased tissue but not to normal tissue; etc.) is desirable in the treatment of tissue specific diseases such as cancer (e.g. prostate cancer). For example, in contrast to systemic delivery of a cytotoxic anti-cancer agent, targeted delivery could prevent the agent from killing healthy cells. Additionally, targeted delivery would allow for the administration of a lower dose of the agent or at a lower administration frequency, which could reduce the undesirable side effects commonly associated with traditional chemotherapy.

In spite of advances in cancer therapy there remains a need for the targeted delivery of highly toxic agents to cancer cells.

SUMMARY OF THE INVENTION

The invention seeks to address the above mentioned need and in one embodiment provides a cytotoxic particle including:
  a core;
  a cytotoxic compound contained in, or entrapped in or on said core;
  a plurality of variable domains arranged on the core for binding to $P2X_7R$ on a cancer cell thereby enabling the particle to bind to a cancer cell having $P2X_7R$ expressed thereon when the particle is contacted with the cancer cell.

In another embodiment there is provided a cytotoxic particle including:
  a liposome;
  a cytotoxic compound contained in, or entrapped in or on said liposome;
  a plurality of variable domains arranged on the liposome for binding to $P2X_7R$ on a cancer cell thereby enabling the particle to bind to a cancer cell having $P2X_7R$ expressed thereon when the particle is contacted with the cancer cell.

In another embodiment there is provided a cytotoxic particle including:
  a liposome;
  a cytotoxic compound in the form of gemcitabine contained in, or entrapped in or on said liposome;
  a plurality of variable domains arranged on the liposome for binding to $P2X_7R$ on a cancer cell thereby enabling the particle to bind to a cancer cell having $P2X_7R$ expressed thereon when the particle is contacted with the cancer cell.

In another embodiment there is provided a cytotoxic particle including:
  a liposome including hydrocarbon chains forming a lipid layer of the liposome;
  a cytotoxic compound in the form of gemcitabine, wherein the primary amine of gemcitabine is bonded to a hydrocarbon chain of the lipid layer via a carbamate group;
  a plurality of variable domains arranged on the liposome for binding to $P2X_7R$ on a cancer cell thereby enabling the particle to bind to a cancer cell having $P2X_7R$ expressed thereon when the particle is contacted with the cancer cell.

In another embodiment there is provided a cytotoxic particle including:
  a liposome including:
    hydrocarbon chains forming a lipid layer of the liposome
    maleimide groups arranged on the liposome enabling conjugation of an antibody thereto;
  a cytotoxic compound in the form of gemcitabine, wherein the primary amine of gemcitabine is bonded to a hydrocarbon chain of the lipid layer via a carbamate group;
  a plurality of variable domains bound to the maleimide groups arranged on the liposome for binding to $P2X_7R$ on a cancer cell thereby enabling the particle to bind to a cancer cell having $P2X_7R$ expressed thereon when the particle is contacted with the cancer cell.

In another embodiment there is provided a cytotoxic particle including:
a liposome including:
  hydrocarbon chains forming a lipid layer of the liposome
  maleimide groups arranged on the liposome enabling conjugation of an antibody thereto;
  a cytotoxic compound in the form of gemcitabine, wherein the primary amine of gemcitabine is bonded to a hydrocarbon chain of the lipid layer via a carbamate group;
  a plurality of variable domains bound to the maleimide groups arranged on the liposome for binding to P2X$_7$R on a cancer cell thereby enabling the particle to bind to a cancer cell having P2X$_7$R expressed thereon when the particle is contacted with the cancer cell,
  wherein the variable domain is defined by Formula 1:

CDR1-CDR2-CDR3 wherein CDR1 is RNHDMG (SEQ ID NO: 4)
wherein CDR2 is AISGSGGSTYYANSVKG (SEQ ID NO: 5)
wherein CDR3 is EPKPMDTEFDY (SEQ ID NO: 6).
Preferably, the variable domain contains framework regions in the formula FR1-CDR1-FR2-CDR2-FR3-CDR3-FR4.

In another embodiment there is provided a cytotoxic particle including:
a liposome including:
  hydrocarbon chains forming a lipid layer of the liposome
  maleimide groups arranged on the liposome enabling conjugation of an antibody thereto;
  a cytotoxic compound in the form of gemcitabine, wherein the primary amine of gemcitabine is bonded to a hydrocarbon chain of the lipid layer via a carbamate group;
  a plurality of variable domains bound to the maleimide groups arranged on the liposome for binding to P2X$_7$R on a cancer cell thereby enabling the particle to bind to a cancer cell having P2X$_7$R expressed thereon when the particle is contacted with the cancer cell,
  wherein the variable domain has the following amino acid sequence (SEQ ID NO: 7):

EVQLLESGGGLVQPGGSLRLSCAASGFTFRNHDMGWVRQAPGKGLEWVSA

ISGSGGSTYYANSVKGRFTISRDNSKNTLYLQMNSLRAEDTAVYYCAEPK

PMDTEFDYRSPGTLVTVSS

In any embodiment, the primary amine of the gemcitabine is covalently bonded to a hydrocarbon chain of the lipid layer. Preferably the primary amine is the cytosine C4 amine of gemcitabine.

In any embodiment of the invention, the liposome is a spherical liposome.

In another embodiment, there is provided a pharmaceutical composition including a plurality of cytotoxic particles mentioned above and a pharmaceutically effective diluent, excipient or carrier. Typically, the pharmaceutical composition is adapted for intravenous administration.

In a further embodiment there is provided a method of treating an individual having cancer including administering a particle or composition mentioned above to the individual, thereby treating the individual for cancer.

In a further embodiment there is provided a method of reducing tumour volume in an individual having cancer comprising administering a particle or composition mentioned above to the individual, thereby reducing tumour volume in the individual.

In a further embodiment there is provided a particle or composition mentioned above for use in the treatment of an individual having cancer.

In a further embodiment, there is provided the use of a particle or composition mentioned above, in the manufacture of a medicament for the treatment of cancer.

In a further embodiment there is provided a method for killing a cancer cell including contacting a cancer cell with a particle or composition mentioned above.

In a further embodiment there is provided a kit including a particle or composition mentioned above.

In any aspect of the present invention, the cytotoxic compound may comprise gemcitabine. Preferably, the gemcitabine is in the form of a conjugate that allows the gemcitabine to be attached to or incorporated in the core or liposome.

In any aspect of the present invention, the core or liposome of the cytotoxic particle is comprised of dioleoylphosphatidylcholine (DOPC).

In any aspect of the present invention, the variable domain may be a single domain antibody or may be part of any other antibody structure as described herein.

Further, the variable domain may be humanized or human.

In any aspect of the present invention, the plurality of variable domains are arranged on the core for selective binding to P2X$_7$R on a cancer cell. Further, the selective binding may be for a P2X$_7$R that is unable to form an apoptotic pore.

Further aspects of the present invention and further embodiments of the aspects described in the preceding paragraphs will become apparent from the following description, given by way of example and with reference to the accompanying drawings.

DETAILED DESCRIPTION OF THE EMBODIMENTS

Figure 1:
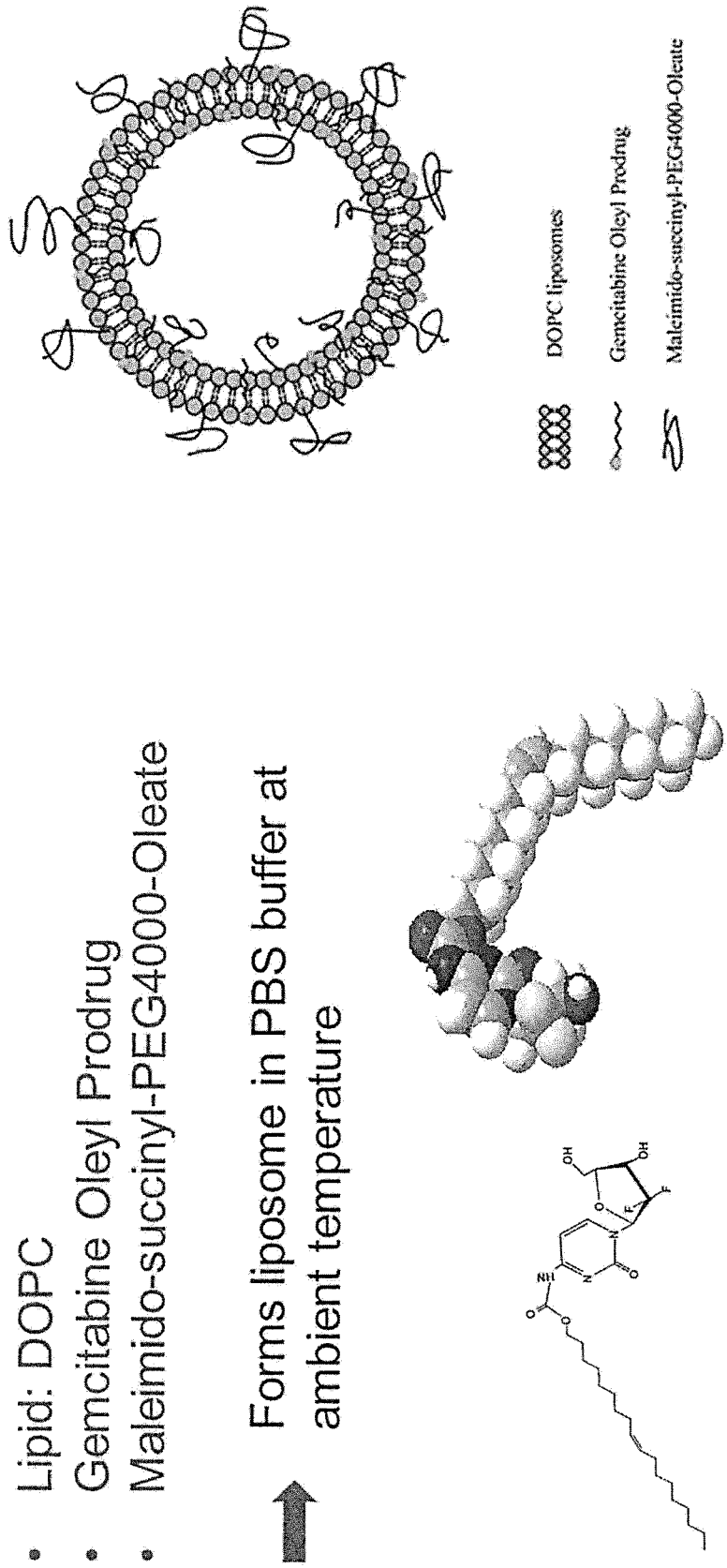
FIG. 1 Cytotoxic nanoparticle formation showing the oleyl-gemcitabine conjugate and formation into a liposome.

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described.

It will be understood that the invention disclosed and defined in this specification extends to all alternative combinations of two or more of the individual features mentioned or evident from the text or drawings. All of these different combinations constitute various alternative aspects of the invention.

All of the patents and publications referred to herein are incorporated by reference in their entirety.

The present invention provides for cytotoxic particles, comprised of a cytotoxic agent and having a plurality of variable domains arranged on the particles, wherein the variable domains allow for binding to $P2X_7R$ on a cancer cell. The particles are able to bind to a cancer cell having $P2X_7R$ expressed thereon when the particle is contacted with the cancer cell.

In certain aspects, the cytotoxic particles of the invention provide for sustained release of the cytotoxic agent, but also provide for reduced toxicity arising from the cytotoxic agent. This is because the variable domains for binding to $P2X_7R$ ensure specificity for binding of the particles to cancerous tissue, and thereby reduce toxicity to healthy, non-cancerous tissue. The present invention therefore provides an advantage over other means of providing cytotoxic agents to cancerous cells.

A. Definitions

For purposes of interpreting this specification, the following definitions will generally apply and whenever appropriate, terms used in the singular will also include the plural and vice versa.

"Purinergic receptor" generally refers to a receptor that uses a purine (such as ATP) as a ligand.

"$P2X_7$ receptor" generally refers to a purinergic receptor formed from three protein subunits or monomers, with at least one of the monomers having an amino acid sequence substantially as shown in SEQ ID NO: 1 below:

```
                                                           SEQ ID NO: 1
  1 MPACCSCSDV FQYETNKVTR IQSMNYGTIK WFFHVIIFSY VCFALVSDKL YQRKEPVISS

61 VHTKVKGIAE VKEEIVENGV KKLVHSVFDT ADYTFPLQGN SFFVMTNFLK TEGQEQRLCP

121 EYPTRRTLCS SDRGCKKGWM DPQSKGIQTG RCVVHEGNQK TCEVSAWCPI EAVEEAPRPA

181 LLNSAENFTV LIKNNIDFPG HNYTTRNILP GLNITCTFHK TQNPQCPIFR LGDIFRETGD

241 NFSDVAIQGG IMGIEIYWDC NLDRWFHHCR PKYSFRRLDD KTTNVSLYPG YNFRYAKYYK

301 ENNVEKRTLI KVFGIRFDIL VFGTGGKFDI IQLVVYIGST LSYFGLAAVF IDFLIDTYSS

361 NCCRSHIYPW CKCCQPCVVN EYYYRKKCES IVEPKPTLKY VSFVDESHIR MVNQQLLGRS

421 LQDVKGQEVP RPAMDFTDLS RLPLALHDTP PIPGQPEEIQ LLRKEATPRS RDSPVWCQCG

481 SCLPSQLPES HRCLEELCCR KKPGACITTS ELFRKLVLSR HVLQFLLLYQ EPLLALDVDS

541 TNSRLRHCAY RCYATWRFGS QDMADFAILP SCCRWRIRKE FPKSEGQYSG FKSPY
```

To the extent that $P2X_7$ receptor is formed from three monomers, it is a "trimer" or "trimeric". "$P2X_7$ receptor" encompasses naturally occurring variants of $P2X_7$ receptor, e.g., wherein the $P2X_7$ monomers are splice variants, allelic variants and isoforms including naturally-occurring truncated or secreted forms of the monomers forming the $P2X_7$ receptor (e.g., a form consisting of the extracellular domain sequence or truncated form of it), naturally-occurring variant forms (e.g., alternatively spliced forms) and naturally-occurring allelic variants. In certain embodiments of the invention, the native sequence $P2X_7$ monomeric polypeptides disclosed herein are mature or full-length native sequence polypeptides comprising the full-length amino acids sequence shown in SEQ ID NO: 1. In certain embodiments the $P2X_7$ receptor may have an amino acid sequence that is modified, for example various of the amino acids in the sequence shown in SEQ ID NO: 1 may be substituted, deleted, or a residue may be inserted.

"Functional $P2X_7$ receptor" generally refers to a form of the $P2X_7$ receptor having three intact binding sites or clefts for binding to ATP. When bound to ATP, the functional receptor forms a non-selective sodium/calcium channel that converts to a pore-like structure that enables the ingress of calcium ions and molecules of up to 900 Da into the cytosol, one consequence of which may be induction of programmed cell death. In normal homeostasis, expression of functional P2X$_7$ receptors is generally limited to cells that undergo programmed cell death such as thymocytes, dendritic cells, lymphocytes, macrophages and monocytes. There may also be some expression of functional P2X$_7$ receptors on erythrocytes and other cell types.

"Non-functional P2X$_7$ receptor" generally refers to a form of a P2X$_7$ receptor having a conformation, distinct from functional P2X$_7$, whereby the receptor is unable to form an apoptotic pore, but which is still able to operate as a non-selective channel through the maintenance of a single functional ATP binding site located between adjacent monomers. One example arises where one or more of the monomers has a cis isomerisation at Pro210 (according to SEQ ID NO: 1). The isomerisation may arise from any molecular event that leads to misfolding of the monomer, including for example, mutation of monomer primary sequence or abnormal post translational processing. One consequence of the isomerisation is that the receptor is unable to bind to ATP at one or two ATP binding sites on the trimer and as a consequence not be able to extend the opening of the channel. In the circumstances, the receptor cannot form a pore and this limits the extent to which calcium ions may enter the cytosol. Non-functional P2X$_7$ receptors are expressed on a wide range of epithelial and haematopoietic cancers.

"Cancer associated-P2X$_7$ receptors" are generally P2X$_7$ receptors that are found on cancer cells (including, pre-neoplastic, neoplastic, malignant, benign or metastatic cells), but not on non-cancer or normal cells.

"E200 epitope" generally refers to an epitope having the sequence GHNYTTNILPGLNITC (SEQ ID NO: 2).

"E300 epitope" generally refers to an epitope having the sequence KYYKENNVEKRTLIK (SEQ ID NO: 3).

"Composite epitope" generally refers to an epitope that is formed from the juxtaposition of the E200 and E300 epitopes or parts of these epitopes.

"Antibodies" or "immunoglobulins" or "Igs" are gamma globulin proteins that are found in blood, or other bodily fluids of verterbrates that function in the immune system to bind antigen, hence identifying and/or neutralizing foreign objects.

Antibodies are generally a heterotetrameric glycoprotein composed of two identical light (L) chains and two identical heavy (H) chains. Each L chain is linked to a H chain by one covalent disulfide bond. The two H chains are linked to each other by one or more disulfide bonds depending on the H chain isotype. Each H and L chain also has regularly spaced intrachain disulfide bridges.

H and L chains define specific Ig domains. More particularly, each H chain has at the N-terminus, a variable domain (VH) followed by three constant domains (CH) for each of the α and γ chains and four CH domains for p and c isotypes. Each L chain has at the N-terminus, a variable domain (VL) followed by a constant domain (CL) at its other end. The VL is aligned with the VH and the CL is aligned with the first constant domain of the heavy chain (CHL).

Antibodies can be assigned to different classes or isotypes. There are five classes of immunoglobulins: IgA, IgD, IgE, IgG, and IgM, having heavy chains designated α, δ, ε, γ, and μ, respectively. The γ and α classes are further divided into subclasses on the basis of relatively minor differences in ¾ sequence and function, e.g., humans express the following subclasses: IgG1, IgG2, IgG3, IgG4, IgA1, and IgA2. The L chain from any vertebrate species can be assigned to one of two clearly distinct types, called kappa and lambda, based on the amino acid sequences of their constant domains.

The constant domain includes the Fc portion which comprises the carboxy-terminal portions of both H chains held together by disulfides. The effector functions of antibodies such as ADCC are determined by sequences in the Fc region, which region is also the part recognized by Fc receptors (FcR) found on certain types of cells.

The pairing of a VH and VL together forms a "variable region" or "variable domain" including the amino-terminal domains of the heavy or light chain of the antibody. The variable domain of the heavy chain may be referred to as "VH." The variable domain of the light chain may be referred to as "VL." The V domain contains an "antigen binding site" which affects antigen binding and defines specificity of a particular antibody for its particular antigen. V regions span about 110 amino acid residues and consist of relatively invariant stretches called framework regions (FRs) (generally about 4) of 15-30 amino acids separated by shorter regions of extreme variability called "hypervariable regions" (generally about 3) that are each generally 9-12 amino acids long. The FRs largely adopt a β-sheet configuration and the hypervariable regions form loops connecting, and in some cases forming part of, the β-sheet structure.

"Hypervariable region" refers to the regions of an antibody variable domain which are hypervariable in sequence and/or form structurally defined loops. Generally, antibodies comprise six hypervariable regions; three in the VH (H1, H2, H3), and three in the VL (L1, L2, L3).

"Framework" or "FR" residues are those variable domain residues other than the hypervariable region residues herein defined.

An "antigen binding site" generally refers to a molecule that includes at least the hypervariable and framework regions that are required for imparting antigen binding function to a V domain. An antigen binding site may be in the form of an antibody or an antibody fragment, (such as a dAb, Fab, Fd, Fv, F(ab')2 or scFv) in a method described herein.

An "intact" or "whole" antibody is one which comprises an antigen-binding site as well as a CL and at least heavy chain constant domains, CH1, CH2 and CH3. The constant domains may be native sequence constant domains (e.g. human native sequence constant domains) or amino acid sequence variant thereof.

"Whole antibody fragments including a variable domain" include Fab, Fab', F(ab')2, and Fv fragments; diabodies; linear antibodies, single-chain antibody molecules; and multispecific antibodies formed from antibody fragments.

The "Fab fragment" consists of an entire L chain along with the variable region domain of the H chain (VH), and the first constant domain of one heavy chain (CHI). Each Fab fragment is monovalent with respect to antigen binding, i.e., it has a single antigen-binding site.

A "Fab' fragment" differs from Fab fragments by having additional few residues at the carboxy terminus of the CHI domain including one or more cysteines from the antibody hinge region. Fab'-SH is the designation herein for Fab' in which the cysteine residue(s) of the constant domains bear a free thiol group.

A "F(ab')2 fragment" roughly corresponds to two disulfide linked Fab fragments having divalent antigen-binding activity and is still capable of cross-linking antigen.

An "Fv" is the minimum antibody fragment which contains a complete antigen-recognition and binding site. This fragment consists of a dimer of one heavy and one light chain variable region domain in tight, non-covalent association.

In a single-chain Fv (scFv) species, one heavy and one light chain variable domain can be covalently linked by a flexible peptide linker such that the light and heavy chains can associate in a "dimeric" structure analogous to that in a two-chain Fv species. From the folding of these two domains emanate six hypervariable loops (3 loops each from the H and L chain) that contribute the amino acid residues for antigen binding and confer antigen binding specificity to the antibody.

"Single-chain Fv" also abbreviated as "sFv" or "scFv" are antibody fragments that comprise the VH and VL antibody domains connected to form a single polypeptide chain. Preferably, the scFv polypeptide further comprises a polypeptide linker between the VH and VL domains which enables the scFv to form the desired structure for antigen binding.

A "single variable domain" is half of an Fv (comprising only three CDRs specific for an antigen) that has the ability to recognize and bind antigen, although at a lower affinity than the entire binding site.

"Diabodies" refers to antibody fragments with two antigen-binding sites, which fragments comprise a heavy-chain variable domain (VH) connected to a light-chain variable domain (VL) in the same polypeptide chain (VH-VL). The small antibody fragments are prepared by constructing sFv fragments (see preceding paragraph) with short linkers (about 5-10 residues) between the VH and VL domains such that interchain but not intra-chain pairing of the V domains is achieved, resulting in a bivalent fragment, i.e., fragment having two antigen-binding sites.

Diabodies may be bivalent or bispecific. Bispecific diabodies are heterodimers of two "crossover" sFv fragments in which the VH and VL domains of the two antibodies are present on different polypeptide chains. Triabodies and tetrabodies are also generally known in the art.

An "isolated antibody" is one that has been identified and separated and/or recovered from a component of its preexisting environment. Contaminant components are materials that would interfere with therapeutic uses for the antibody, and may include enzymes, hormones, and other proteinaceous or nonproteinaceous solutes.

A "human antibody" refers to an antibody that possesses an amino acid sequence that corresponds to that of an antibody produced by a human. Human antibodies can be produced using various techniques known in the art, including phage-display libraries. Human antibodies can be prepared by administering the antigen to a transgenic animal that has been modified to produce such antibodies in response to antigenic challenge, but whose endogenous loci have been disabled.

"Humanized' forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin.

"Monoclonal antibody" refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site or determinant on the antigen. In addition to their specificity, the monoclonal antibodies are advantageous in that they may be synthesized uncontaminated by other antibodies. Monoclonal antibodies may be prepared by the hybridoma methodology. The "monoclonal antibodies" may also be isolated from phage antibody libraries using molecular engineering techniques.

The term "anti-P2X$_7$ receptor antibody" or "an antibody that binds to P2X$_7$ receptor" refers to an antibody that is capable of binding P2X$_7$ receptor with sufficient affinity such that the antibody is useful as a diagnostic and/or therapeutic agent in targeting P2X$_7$ receptor, typically non-functional P2X$_7$ receptor or a cancer associated P2X$_7$ receptor. Preferably, the extent of binding of an P2X$_7$ receptor antibody to an unrelated protein is less than about 10% of the binding of the antibody to P2X$_7$ receptor as measured, e.g., by a radioimmunoassay (RIA), Enzyme-Linked Immunosorbent Assay (ELISA), Biacore or Flow Cytometry. In certain embodiments, an antibody that binds to P2X$_7$ receptor has a dissociation constant (Kd) of <1 µM, <100 nM, <10 nM, <1 nM, or <0.1 nM. An anti non-functional P2X$_7$ receptor antibody is generally one having some or all of these serological characteristics and that binds to non-functional P2X$_7$ receptors but not to functional P2X$_7$ receptors.

An "affinity matured' antibody is one with one or more alterations in one or more hypervariable region thereof that result in an improvement in the affinity of the antibody for antigen, compared to a parent antibody that does not possess those alteration(s). Preferred affinity matured antibodies will have nanomolar or even picomolar affinities for the target antigen. Affinity matured antibodies are produced by procedures known in the art.

A "blocking" antibody" or an "antagonist" antibody is one that inhibits or reduces biological activity of the antigen it binds. Preferred blocking antibodies or antagonist antibodies substantially or completely inhibit the biological activity of the antigen.

An "agonist antibody", as used herein, is an antibody, which mimics at least one of the functional activities of a polypeptide of interest.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity, which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention.

"Epitope" generally refers to that part of an antigen that is bound by the antigen binding site of an antibody. An epitope may be "linear" in the sense that the hypervariable loops of the antibody CDRs that form the antigen binding site bind to a sequence of amino acids as in a primary protein structure. In certain embodiments, the epitope is a "conformational epitope" i.e. one in which the hypervariable loops of the CDRs bind to residues as they are presented in the tertiary or quaternary protein structure.

'Treatment' generally refers to both therapeutic treatment and prophylactic or preventative measures.

Subjects requiring treatment include those already having a benign, pre-cancerous, or non-metastatic tumour as well as those in which the occurrence or recurrence of cancer is to be prevented.

The objective or outcome of treatment may be to reduce the number of cancer cells; reduce the primary tumour size; inhibit (i.e., slow to some extent and preferably stop) cancer cell infiltration into peripheral organs; inhibit (i.e., slow to some extent and preferably stop) tumour metastasis; inhibit, to some extent, tumour growth; and/or relieve to some extent one or more of the symptoms associated with the disorder.

Efficacy of treatment can be measured by assessing the duration of survival, time to disease progression, the response rates (RR), duration of response, and/or quality of life.

"Pre-cancerous" or "pre-neoplasia" generally refers to a condition or a growth that typically precedes or develops into a cancer. A "pre-cancerous" growth may have cells that are characterized by abnormal cell cycle regulation, proliferation, or differentiation, which can be determined by markers of cell cycle.

Other examples of cancer include blastoma (including medulloblastoma and retinoblastoma), sarcoma (including liposarcoma and synovial cell sarcoma), neuroendocrine tumours (including carcinoid tumours, gastrinoma, and islet cell cancer), mesothelioma, schwannoma (including acoustic neuroma), meningioma, adenocarcinoma, melanoma, leukemia or lymphoid malignancies, lung cancer including small-cell lung cancer (SGLG), non-small cell lung cancer (NSGLG), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer (including metastatic breast cancer), colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophagael cancer, tumours of the biliary tract, as well as head and neck cancer.

"A condition or symptom associated' [with the cancer] may be any pathology that arises as a consequence of, preceding, or proceeding from the cancer. For example, where the cancer is a skin cancer, the condition or relevant symptom may be microbial infection. Where the cancer is a secondary tumour, the condition or symptom may relate to organ dysfunction of the relevant organ having tumour metastases. In one embodiment, the methods of treatment described herein are for the minimisation or treatment of a condition or symptom in an individual that is associated with a cancer in the individual.

As used herein, except where the context requires otherwise, the term "comprise" and variations of the term, such as "comprising", "comprises" and "comprised", are not intended to exclude further additives, components, integers or steps. The terms "including" and "comprising" may be used interchangeably.

B. Cytotoxic Particles

In one embodiment there is provided a cytotoxic particle including:
a core
a cytotoxic compound contained in, or entrapped in or on said core;
a plurality of variable domains arranged on the core for binding to $P2X_7$ receptors on a cancer cell, the arrangement enabling the particle to cross link $P2X_7$ receptors on a cancer cell when the particle is contacted with a cancer cell.

B.1 Core

The core may generally define the overall dimensions and physical characteristics of the particle.

The core may be formed from lipid, protein, sugar or other biomolecule. Alternatively, the core may be formed of a polymer, resin, plastic or ceramic or glass.

In one particularly preferred embodiment the core is provided in the form of a liposome, micelle, microemulsion or macroemulsion.

Micelles are colloidal aggregates of amphipathic (surfactant) molecules that are formed at a well-defined concentration known as the critical micelle concentration. Micelles are oriented with the nonpolar portions at the interior and the polar portions at the exterior surface, exposed to water. The typical number of aggregated molecules in a micelle (aggregation number) is 50 to 100.

Microemulsions are essentially swollen micelles, although not all micellar solution can be swollen to form microemulsion. Microemulsions are thermodynamically stable, are formed spontaneously, and contain particles that are extremely small. Droplet diameters in microemulsions typically range from 10-100 nm.

Macroemulsions are droplets with diameters greater than 100 nm.

Liposomes are closed lipid vesicles comprising lipid bilayers that encircle aqueous interiors. Liposomes typically have diameters of 25 nm to 1 µm (see, e.g., D. O. Shah (ed), 1998, Micelles, Microemulsions, and Monolayers: Science and Technology, Marcel Dekker; A. S. Janoff (ed), 1998, Liposomes: Rational Design, Marcel Dekker).

Preferably the core is provided in the form of a liposome. In this embodiment, the particle may be described as an antibody-liposome conjugate.

The liposome may consist of lipids including phosphoglycerides and sphingolipids, representative examples of which include phosphatidylcholine, phosphatidylethanolamine, phosphatidylserine, phosphatidylinositol, phosphatidic acid, palmitoyloleoyl phosphatidylcholine, lysophosphatidylcholine, lysophosphatidyl-ethanolamine, dipalmitoylphosphatidylcholine, dioleoylphosphatidylcholine, distearoyl-phosphatidylcholine or dilinoleoylphosphatidylcholine. Other compounds lacking in phosphorus, such as sphingolipid and glycosphingolipid families are also contemplated. Additionally, the amphipathic lipids described above may be mixed with other lipids including triacyglycerols and sterols.

The liposome may have a diameter ranging between about 50 nm and 200 µm. Accordingly, the liposome may be a small, sonicated unilamellar vesicle (SUV), a large unilamellar vesicle (LUV), or a liposome prepared by reverse phase evaporation (a REV), by French press (a FPV) or by ether injection (an EIV). Methods of preparing liposomes of such sizes, including methods of fractionating and purifying liposomes of the desired size, are known to one skilled in the art. Typically, the liposome has a diameter ranging between about 10 and 600 nm. In one embodiment, the liposome has a diameter of between about 50 and 200 nm. In one embodiment, the liposome is a LUV.

Typically, the liposome of the invention is a unilamellar with respect to the liposome lipid bilayer. However, it will be understood that the liposome of the invention may comprise more than one lipid bilayer. Thus in one embodiment, the liposome may be a multilamellar vesicle such as a large, vortexed multilamellar vesicle (MLV).

As described herein a compound for providing the liposome with a charge for binding the liposome to a cancer cell is advantageous for improving the fusion between the cancer cell lipid bilayer and the liposome bilayer. For example, DOTAP is particularly useful as a binding means for binding the liposome lipid bilayer to a target cell.

The liposome may be adapted for destabilisation of the liposome lipid bilayer at the pH of an early endosome. An early endosome is a vacuole or vesicle formed at an early stage of the endocytotic pathway. This organelle typically has a pH ranging from 5.5 to 6.0.

Liposomes can be constructed by well-known techniques (see, e.g., G. Gregoriadis (ed.), 1993, Liposome Technology Vols. 1-3, CRC Press, Boca Raton, FL). Lipids are typically dissolved in chloroform and spread in a thin film over the surface of a tube or flask by rotary evaporation. If liposomes comprised of a mixture of lipids are desired, the individual components are mixed in the original chloroform solution. After the organic solvent has been eliminated, a phase consisting of water optionally containing buffer and/or electrolyte is added and the vessel agitated to suspend the lipid. This mixture can then be emulsified by the use of a homogenizer, lyophilized, and melted to obtain multilamellar liposomes. Alternatively, unilameilar liposomes can be produced by the reverse phase evaporation method (Szoka and Papahadjopoulos, 1978, Proc. Natl. Acad. Sci. USA 75:4194-4198). Unilameilar vesicles can also be prepared by sonication or extrusion. Sonication is generally performed with a bath-type sonifier, such as a Branson tip sonifier (G. Heinemann Ultrashall and Labortechnik, Schwabisch Gmund, Germany) at a controlled temperature as determined by the melting point of the lipid. Extrusion may be carried out by biomembrane extruders, such as the Lipex Biomembrane Extruder (Northern Lipids Inc, Vancouver, British Columbia, Canada). Defined pore size in the extrusion filters may generate unilameilar liposomal vesicles of specific sizes. The liposomes can also be formed by extrusion through an asymmetric ceramic filter, such as a Ceraflow Microfilter (commercially available from the Norton Company, Worcester, MA).

Following liposome preparation, the liposomes that have not been sized during formation may be sized by extrusion to achieve a desired size range and relatively narrow distribution of liposome sizes. A size range of about 0.1-0.5 microns will allow the liposome suspension to be sterilized by filtration through a conventional filter (e.g., a 0.22 micron filter or other filter). The filter sterilization method can be carried out on a high throughput basis.

Several techniques are available for sizing liposomes to a desired size, including, ultrasonication, high-speed homogenization, and pressure filtration (M. J. Hope et al., 1985, Biochimica et Biophysica Acta 812:55; U.S. Pat. Nos. 4,529,561 and 4,737,323). Sonicating a liposome suspension either by bath or probe sonication produces a progressive size reduction down to small unilameilar vesicles less than about 0.05 microns in size. Multilamellar vesicles can be recirculated through a standard emulsion homogenizer until selected liposome sizes, typically between about 0.1 and 0.5 microns, and preferably between about 0.1 and 0.2 microns. The size of the liposomal vesicles may be determined by quasi-elastic light scattering (QELS) (see Bloomfield, 1981, Ann. Rev. Biophys. Bioeng. 10:421-450). Average liposome diameter may be reduced by sonication of formed liposomes. Intermittent sonication cycles may be alternated with QELS assessment to guide efficient liposome synthesis.

Liposomes can be extruded through a small-pore polycarbonate membrane or an asymmetric ceramic membrane to yield a well-defined size distribution. Typically, a suspension is cycled through the membrane one or more times until the desired liposome size distribution is achieved. The liposomes may be extruded through successively smaller-pore membranes, to achieve a gradual reduction in liposome size.

In a particularly preferred embodiment, the cytotoxic particle includes a core in the form of a liposome, wherein the liposome includes oleic acid fatty acid chains in a lipid layer of the liposome. The core is preferably in the form of spherical bilayer membranes to form the liposome. The oleic acid may be functionalised to form a carbamate group for binding to gemcitabine, or functionalised with maleimido groups for binding to an immunoglobulin domain. Preferably the liposomes have a size of about 60 to 150 nm.

B.2 Variable Domains

The variable domains arranged on the core for binding to $P2X_7$ receptors on a cancer cell may be provided in the form of a whole antibody, or a fragment of an antibody that includes a variable domain.

In one embodiment, the variable domains are for binding to cancer associated-$P2X_7$ receptors.

In another embodiment, the variable domains are for binding to non-functional $P2X_7$ receptors.

In one embodiment, the variable domain is one that discriminates between functional and non-functional $P2X_7$ receptors, so as to bind to non-functional receptors, but not to functional receptors. Examples of variable domains are those that bind to the E200 epitope, E300 epitope or composite epitope as for example in PCT/AU2002/000061, PCT/AU2002/001204, PCT/AU2007/001540, PCT/AU2007/001541, PCT/AU2008/001364, PCT/AU2008/001365, PCT/AU2009/000869 and PCT/AU2010/001070, all of which are incorporated by reference.

Fragments of variable domains include single chain antibodies, single chain Fv fragments, and F(ab')2, Fab, Fd and Fv fragments.

The variable domains may arise from monoclonal or polyclonal antiserum.

The variable domains may be human, humanised, chimeric, mouse, rat, rabbit or other mammalian species.

The variable domain may be affinity matured.

The antibodies in which the variable domains are arranged may have multiple specificities or valencies.

The variable domain may be adapted so as to be suited to administration by a selected method.

The variable domain may be provided in an antibody of any isotype. The antibody may be produced by hybridoma, or by recombinant expression, or may be obtained from serum for example as obtainable from a mammal, particularly a human or mouse. The antibody may also be obtained from an avian.

In a particularly preferred embodiment, the variable domain is defined by Formula 1:

CDR1-CDR2-CDR3 wherein CDR1 is RNHDMG (SEQ ID NO: 4)
wherein CDR2 is AISGSGGSTYYANSVKG (SEQ ID NO: 5)
wherein CDR3 is EPKPMDTEFDY (SEQ ID NO: 6)

In a particularly preferred embodiment, the variable domain has the following amino acid sequence (SEQ ID NO: 7):

EVQLLESGGGLVQPGGSLRLSCAASGFTFRNHDMGWVRQAPGKGLEWVSA

ISGSGGSTYYANSVKGRFTISRDNSKNTLYLQMNSLRAEDTAVYYCAEPK

PMDTEFDYRSPGTLVTVSS or (SEQ ID NO: 8)
EVQLLESGGGLVQPGGSLRLSCAASGFTFRNHDMGWVRQAPGKGLEWVSA

ISGSGGSTYYADSVKGRFTISRDNSKNTLYLQMNSLRAEDTAVYYCAEPK

PMDTEFDYRSPGTLVTVSS.

B.3 Conjugation of Variable Domains to Liposomes

The variable domains or antibodies can be conjugated to liposomes using conventional techniques (see, e.g., M. J. Ostro (ed.) 1987, Liposomes: from Biophysics to Therapeutics, Marcel Dekker, New York, NY). One preferred method of preparing liposomes and conjugating immunoglobulins to their surface is described by Y. Ishimoto et al., 1984, J. Immunol. Met. 75:351-360. In accordance with this method, multilamillar liposomes composed of dipalmitoylphosphatidylcholine, cholesterol, and phosphotidylethanolamine are prepared. Purified fragments are then coupled to the phosphatidylethanolamine by the cross-linking agent N-hydroxysuccinimidyl 3-(2-pyridyldithio) propionate. The coupling of the antibody or fragment to the liposome is demonstrated by the release of a pre-trapped marker, e.g., carboxyfluorescence, from the liposomes. This release occurs upon incubation with a secondary antibody against the conjugated antibody, fragment, or complement.

The variable domains and antibodies can also be coupled to a liposome or another carrier of the invention via carbohydrate moieties. Such coupling can be used provided that the carbohydrate moiety is not in the hypervariable region or at the antibody binding sites. In this way, conjugation via the cross-linking with the carbohydrate will not affect binding, and the binding sites will still be available to bind to cell surface antigens. One preferred method for coupling antibodies or antibody fragments of the invention (other than Fv) to a polymer backbone or a liposome involves conjugation through the carbohydrate moieties in the constant regions. This maximizes the number of available antigen-binding sites. Methods for derivatizing sugar ring moieties to create hydrazide groups for coupling with antibody fragments (and antibodies) have been established (see J. D. Rodwell et al., 1986, Proc. Natl. Acad. Sci. USA 83:2632-36). Several immunoconjugates prepared in this way are in clinical studies or pending approval for routine clinical uses.

Binding of a monoclonal antibody to the surface of a liposome may also be accomplished by the formation of cross-linkage between phosphatidylethanolamine and the antibody using glutaraldehyde. Similarly, the targeting antibody may be cross-linked to the liposome via a reactive PEG group anchored on the surface of the liposome and acting as a stealth coating.

Alternatively, a thiolated antibody can be allowed to react with a liposome comprising a lipid into which a maleimide group has been incorporated. Remaining maleimide groups on the surface of the liposome may be further reacted with a compound containing thiolated polyalkyleneglycol moiety. Thiolation of an antibody or antibody fragment may be achieved through use of N-succinimidyl-3-(2-pyridyldithio) propionate (SPDP), which is usually used for thiolation of protein, iminothiolane, or mercaptoalkylimidate. Alternatively, a dithiol group endogenous to an antibody may be reduced to form a thiol group. The latter method is preferred for maintaining antibody function. In accordance with another method, whole antibodies are treated with an enzyme such as pepsin to form F(ab)2 fragments, which are then reduced with dithiothreitol (DTT) to form Fab fragments, which results in the production of one to three thiol groups. The conjugation of the thiolated antibody to the maleimide group-containing liposome may be accomplished by reacting the components in a neutral buffer solution at pH 6.5-7.5 for 2-16 hours.

B. 3 Cytotoxic Drugs

Preferably the cytotoxic drug is a nucleoside analogue that, when incorporated into a nucleic acid strand during replication leads to apoptosis.

Preferably the nucleoside analogue is a pyrimidine.

The pyrimidine may be selected from gemcitabine (4-amino-1-(2-deoxy-2,2-difluoro-β-D-erythro-pentofuranosyl)pyrimidin-2(1H)-on) (Gemzar). or cytarabine (4-amino-1-[(2R,3S,4S,5R)-3,4-dihydroxy-5-(hydroxymethyl) oxolan-2-yl]-1,2-dihydro pyrimidin-2-one or ara-C), Preferably the pyrimidine is gemcitabine.

B. 4 Conjugation of Cytotoxic Drugs to Liposome

Generally a cytotoxic drug may be conjugated to a liposome by functionalising a lipid component for forming a lipid layer of the liposome and then reacting the functional group with a cytotoxic agent so as to form a lipid-drug conjugate. The drug conjugate is then mixed with other lipid components and conditions applied for formation of a liposome as described above. In one embodiment an oleic acid hydrocarbon fatty acid chain is functionalised enabling the formation of a carbamate group between the cytotoxic agent and the oleic acid.

C. Pharmaceutical Compositions & Cancer Therapy

In one embodiment there is provided a pharmaceutical composition including a plurality of cytotoxic particles according to the invention and a pharmaceutically effective diluent, excipient or carrier. In one embodiment, the particle for use in the composition has a core in the form of a liposome.

The particles of the composition may have the same density of variable domains.

The core of each particle in the composition may have the same surface area

In one embodiment there is provided a method of treating an individual for a cancer, especially a cancer including cancer cells that have a low copy number or low expression or production of cell surface $P2X_7R$, including providing a therapeutically effective amount of a particle or composition mentioned above to the individual, thereby treating the individual for cancer. In this embodiment there is provided a particle or composition mentioned above for use in the treatment of an individual having cancer, wherein the cancer includes cancer cells that have a low copy number or low expression or production of cell surface $P2X_7R$.

The particles or compositions of the invention may be administered to a subject in need thereof by oral, parenteral (e.g. intravenous, intra-arterial, intraperitoneal, intramuscular, subcutaneous, intradermal, rectal or vaginal) route, by inhalation or topical application. One form for administration would be a solution for injection, in particular for intravenous or intra-arterial injection or drip, comprising a buffer (e.g. acetate, phosphate or citrate buffer), a surfactant (e.g. polysorbate), optionally a stabilizer agent (e.g. human albumin). In other methods particles can be delivered directly to the site of disease thereby increasing the exposure of the diseased cell or tissue to the antibody.

Preparations for parenteral administration includes sterile aqueous (aqueous carriers include water, alcoholic/aqueous solutions, emulsions or suspensions, including saline and buffered media) or non-aqueous (non-aqueous solvents are propylene glycol, polyethylene glycol, vegetable oils such as olive oil, and injectable organic esters such as ethyl oleate) solutions, suspensions, and emulsions. Pharmaceutically acceptable carriers include between 0.01 to 0.1 M and preferably 0.05 M phosphate buffer or 0.9% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions, in such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Suitable formulations for use in the therapeutic methods disclosed herein are described in Remington's Pharmaceutical Sciences, Mack Publishing Co., 16th ed. (1980).

Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminium monostearate and gelatine.

In any case, sterile injectable solutions can be prepared by incorporating a particle of the invention in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying, freeze-drying and spray drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit. Such articles of manufacture will preferably have labels or package inserts indicating that the associated compositions are useful for treating a subject suffering from, or predisposed to disorders.

Effective doses of the compositions of the present invention, for treatment of disorders, as described herein, vary depending upon many different factors, including means of administration, target site, physiological state of the patient, whether the patient is human or an animal, other medications administered, and whether treatment is prophylactic or therapeutic. Treatment dosages may be titrated using routine methods known to those of skill in the art to optimize safety and efficacy.

The particles of the invention can be administered before, during or after surgical intervention for resection or removal of tumour or tissue.

In one embodiment, the method is particularly useful for delaying disease progression.

In one embodiment, the method is particularly useful for extending survival of the human, including overall survival as well as progression free survival.

In one embodiment, the method is particularly useful for providing a complete response to therapy whereby all signs of cancer in response to treatment have disappeared. This does not always mean the cancer has been cured.

In one embodiment, the method is particularly useful for providing a partial response to therapy whereby there has been a decrease in the size of one or more tumours or lesions, or in the extent of cancer in the body, in response to treatment.

In one embodiment, the cancer is pre-cancerous or pre-neoplastic.

In one embodiment, the cancer is a secondary cancer or metastases. The secondary cancer may be located in any organ or tissue, and particularly those organs or tissues having relatively higher hemodynamic pressures, such as lung, liver, kidney, pancreas, bowel and brain.

D. Assays for Activity

The activities of the particles of the invention may be measured in vitro with reference to various cell function parameters including cytotoxicity, cytostasis, apoptosis induction, cell morphology, cytokine production, signal transduction, cell proliferation and activation status and protein expression and activation. Other biologically appropriate endpoints may also be considered.

In some particular embodiments of the invention activity may be assessed by means of a MTT assay or XTT assay (cell proliferation); a trypan blue exclusion assay (cell viability); membrane phosphoserine asymmetry, annexin 5 binding and caspase assays (apoptosis); and cytokine production (cell function).

The assay may employ a cell line expressing $P2X_7R$. Preferably cell lines having high copy number, or production or expression of $P2X_7R$ (such as PC3, discussed below) and cells having low copy number or production or expression of $P2X_7R$ (such as COLO25, discussed below) are utilised.

In one embodiment, these assays may be particularly useful for determining the amount of variable domain to arrange on the core of the particle.

EXAMPLES

Example 1: Liposome Formation

The manufacture of immunoliposomes consists of two main parts: nanoparticle construction and antibody conjugation.

Nanoparticle construction: Nanoparticles recipients are DOPC (from Avanti Polar Lipids), Gem-Ole (synthesised by reaction oleyl cholorfomate to the hydroxyl-protected Gemcitabine base via carbamate chemical linkage, SOP-Syn001-002) and Maleimido-Succinyl-PEG4000-Oleate (synthesised by converting Succinyl PEG4000-Oleate to Maleimido-Succinyl-PEG4000-Oleate, SOP-Syn 003-005). 43% DOPC, 30% Gem Ole and 27% Maleimido-Succinyl-PEG4000-Oleate are dissolved in EtOH and a thin film is generated through rotary evaporation. The thin film is further hydrated with 1×PBS to the concentration of 10 mg/mL. The hydrated nanoparticle solution is sonicated for 2 min then passed through a 200 nm membrane three times and a 100 nm membrane six times to yield a translucent nanoparticle solution with the average size of 50-100 nm mean diameter.

Antibody conjugation: The antibody is activated via Traut's reagent prior to mixing with nanoparticle solution. The conjugated nanoparticles are quenched with L-cysteine and purified via tangential flow filtration. The immunoliposomes are then further extruded through a 100 nm membrane three times and followed by sterile filtration through a 200 nm membrane. The antibody used herein was a single domain antibody. The single domain antibody comprised the CDR sequences as shown in SEQ ID NOs: 4, 5 and 6. Further, the variable domain comprised the amino acid sequence as shown in SEQ ID NO: 7.

Figure 2:
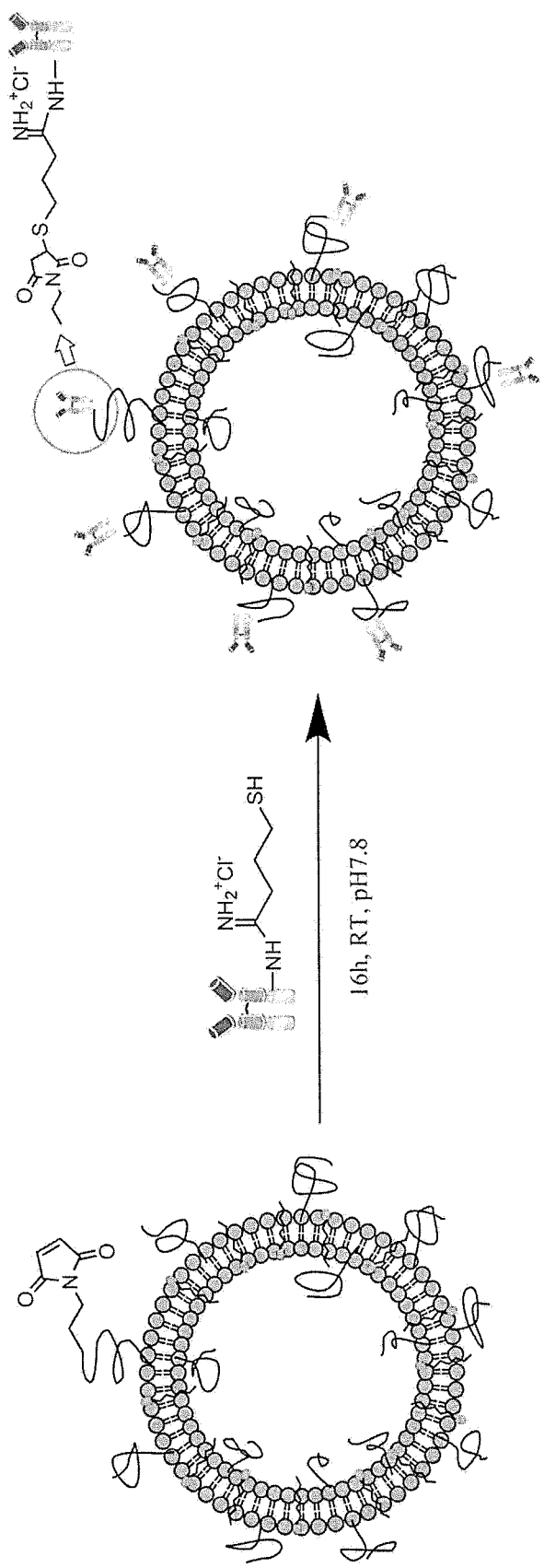
FIG. 2 Conjugation of antibody variable domains to liposome via maleimide groups.
Figure 3:
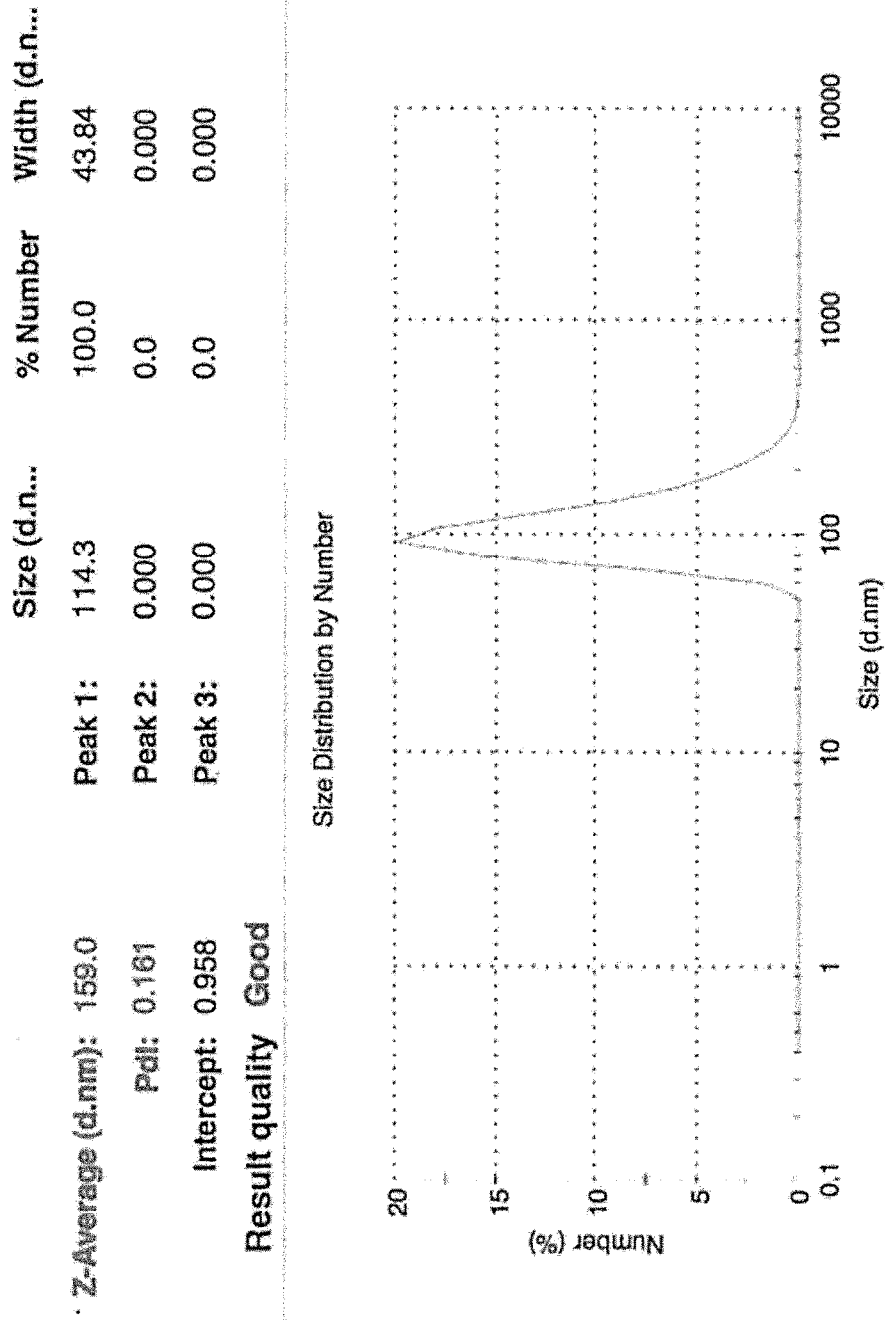
FIG. 3 Size distribution of liposomes.

FIG. 1 is a schematic of the cytotoxic nanoparticle formation showing the oleyl-gemcitabine conjugate and formation into a liposome. FIG. 2 shows conjugation of antibody variable domains to liposomes via maleimide groups. FIG. 3 shows the size distribution of the liposomes.

Example 2: Binding Specificity of Cytotoxic Nanoparticles

Figure 5:
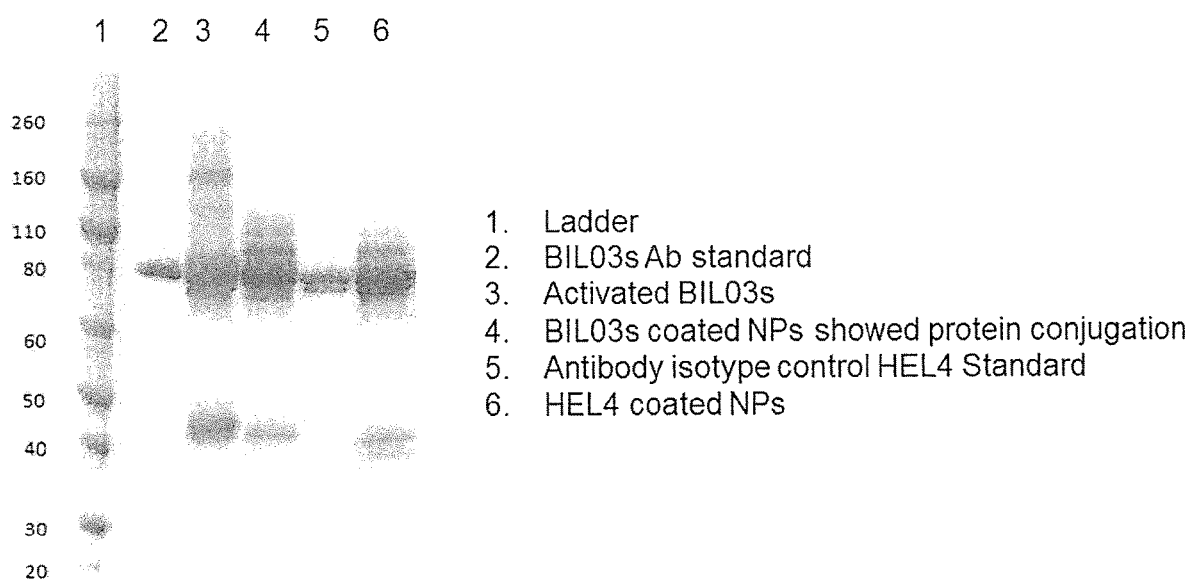
FIG. 5 Conjugation of antibody to liposome demonstrated by SDS PAGE gel. Nupage 4-12% Bis tris gel, MOPS buffer (1×). The gel was run at 180V for 55 mins.

Conjugation of antibody to liposome was demonstrated by SDS PAGE gel Nupage 4-12% Bis tris gel, MOPS buffer (1×) (see FIG. 5).

Figure 4:
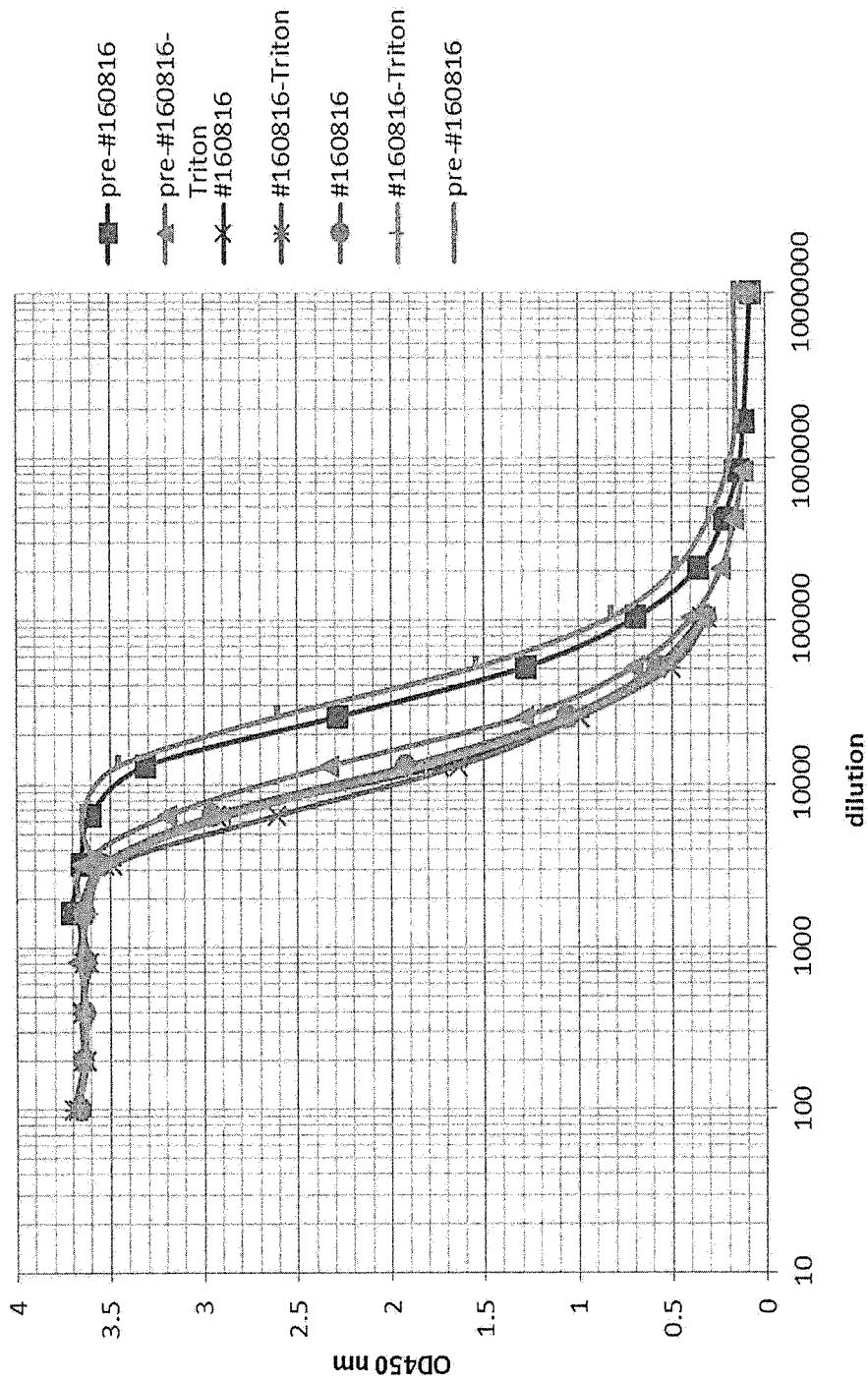
FIG. 4 Serological binding of liposomes by ELISA. Protein concentration after tangential flow filtration (TFF) washing is in the range of 400 to 500 µg/m L.

The liposomes of the invention were also assessed for their ability to bind to the E200 epitope of $P2X_7R$. The results (by ELISA, and shown in FIG. 4), demonstrate that the nanoparticles have particle affinity for the E200 epitope. Accordingly, the liposomes of the invention provide for selective binding to cancerous cells expressing non-functional $P2X_7R$.

Example 3: Biodistribution Imaging of Fluorescently Labelled Nanoparticles in 4T1-Luc2 Tumour Bearing Mice The near-infrared (NIR) lipophilic fluorescent dye DiR (ThermoFisher) was incorporated into the lipid bilayer of naked nanoparticles, nanoparticles coated with HEL4 (isotype) and nanoparticles coated with variable domains for binding to anti-$P2X_7R$ ($P2X_7$-binding domain-coated nanoparticles, or "BIL03s-coated"). Female Balb/c mice were inoculated orthotopically ($4^{th}$ mammary fat pad) with 4T1-luc2 murine breast cancer cells. A 50 μL dose of nanoparticles was injected intravenously at study day 0 and near-infrared (NIR) imaging was performed at 6, 12, 24, 48 and 96 post treatment. At termination, excised liver, spleen and tumour NIR imaging was performed and bioluminescence imaging was performed on tumour tissues.

Figure 6:
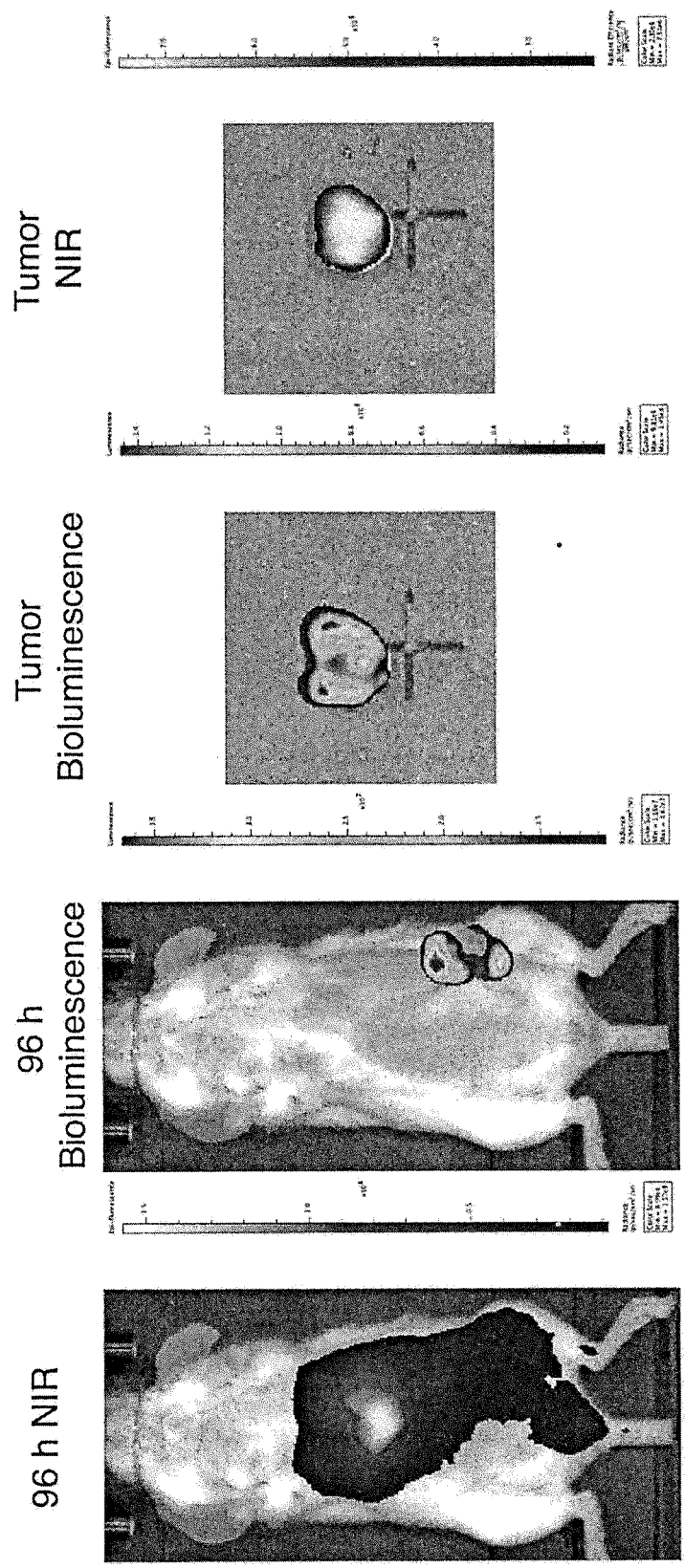
FIG. 6 Selective localisation of cytotoxic particles to 4T1 tumours.
Figure 7:
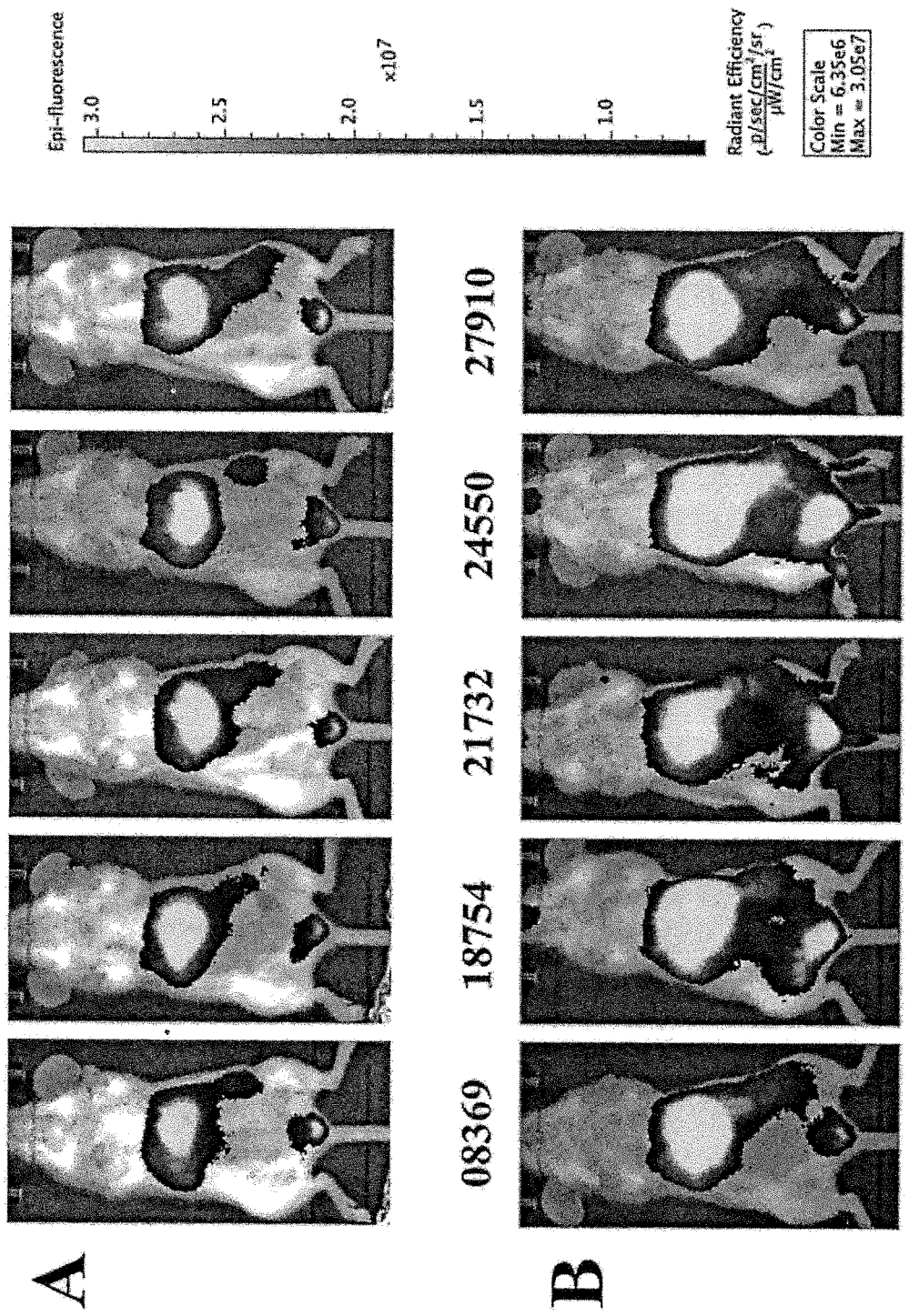
FIG. 7 Whole animal NIR imaging, revealing that (B) antibody-conjugated cytotoxic particles are retained in the tumour much longer than (A) non antibody-conjugated particles.
Figure 9:
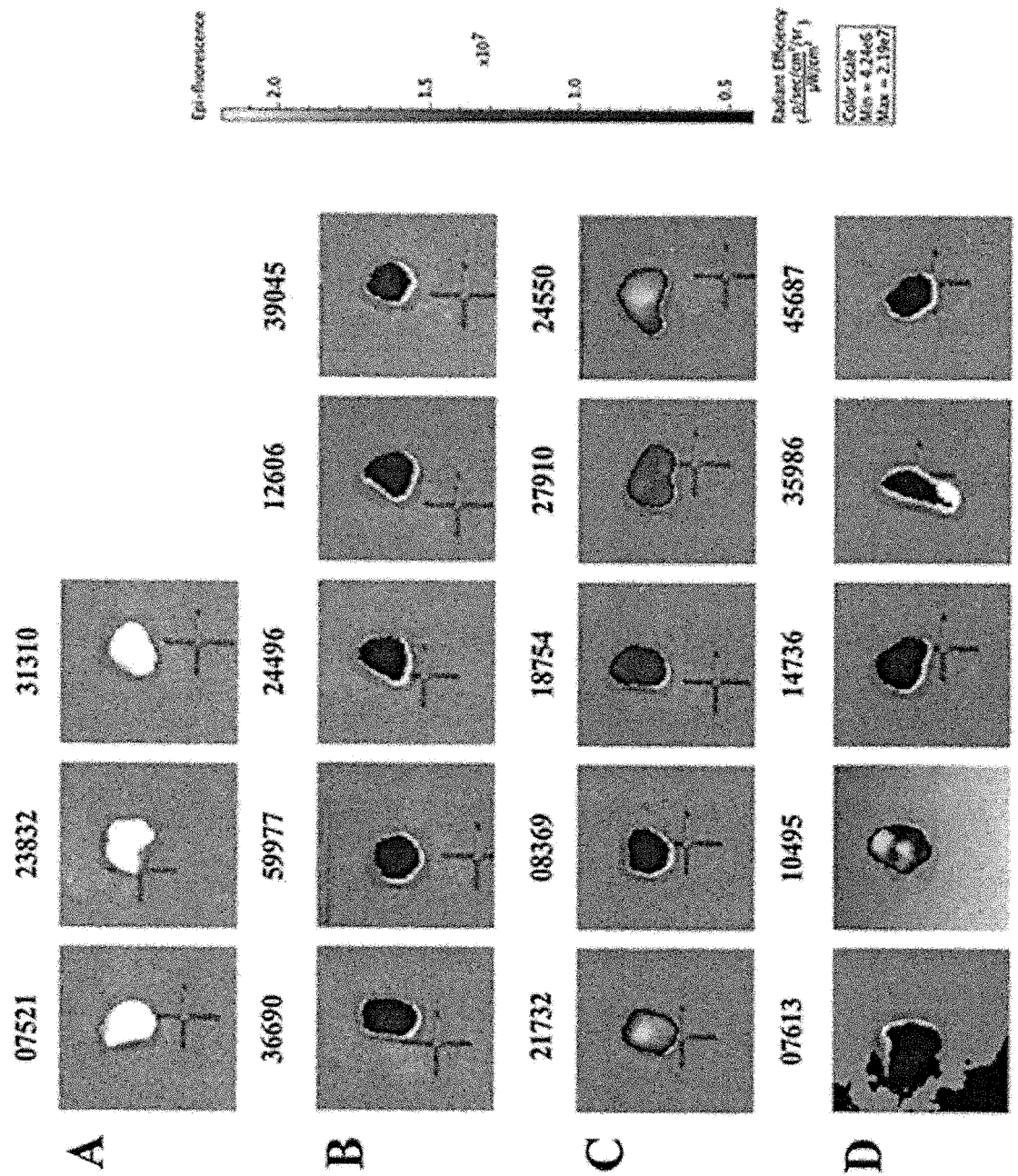
Figure 9:
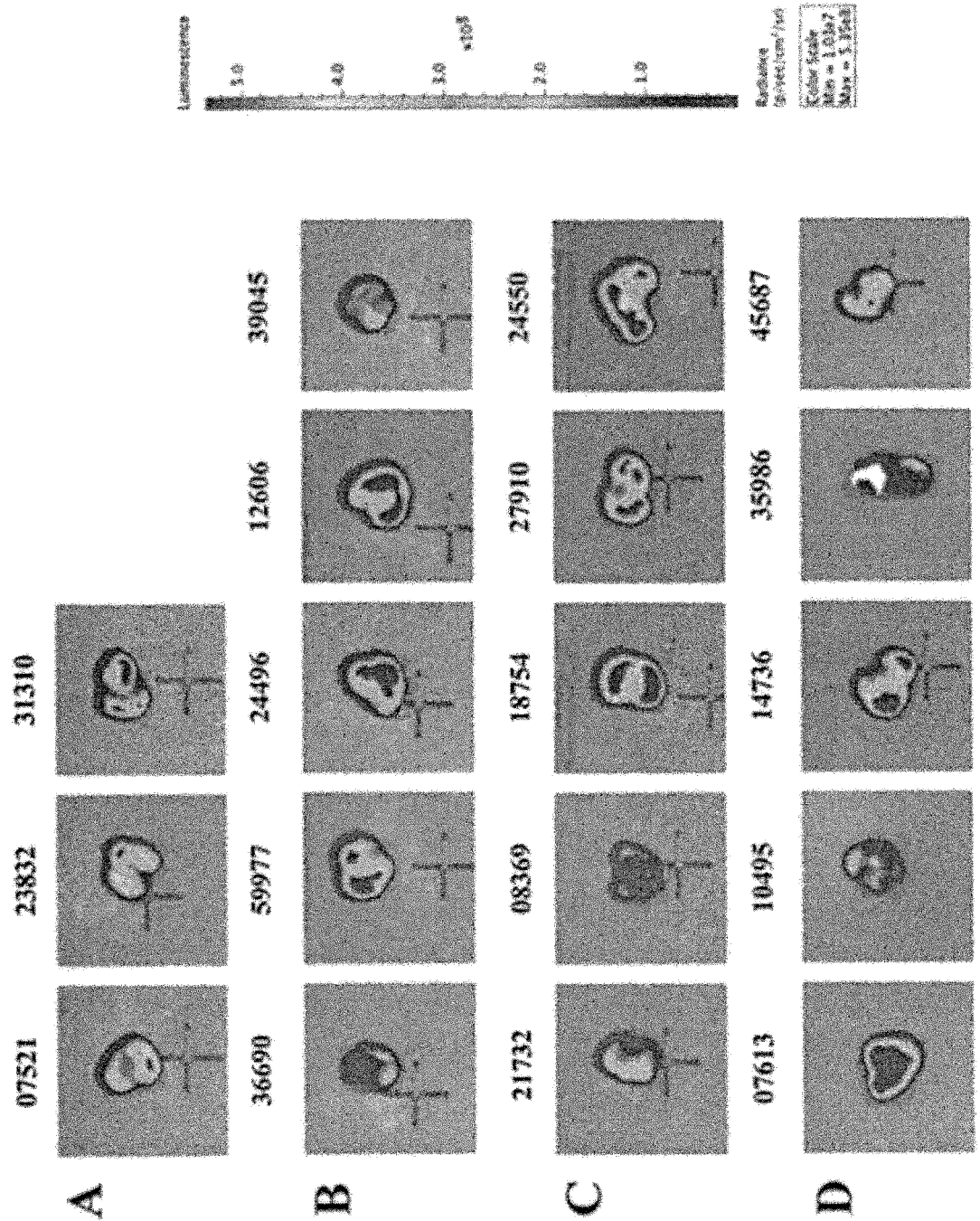

Whole animal NIR imaging and ex vivo bioluminescence showed that there was greater accumulation in tumours of nanoparticles coated with $P2X_7R$-binding domains (BIL03s) than control nanoparticles (either naked particles or HEL4-coated) (see FIGS. 6 and 7). In particular, FIG. 6 shows selective localisation of cytotoxic particles to 4T1 tumours. Antibody-conjugated cytotoxic particle accumulation in the tumour is much greater than for non-antibody-conjugated particles (FIGS. 7 and 9). Specifically, FIG. 9 shows by ex vivo bioluminescence imaging that antibody coated nanoparticles had higher accumulation in the excised tumour than naked nanoparticles.

Figure 8:
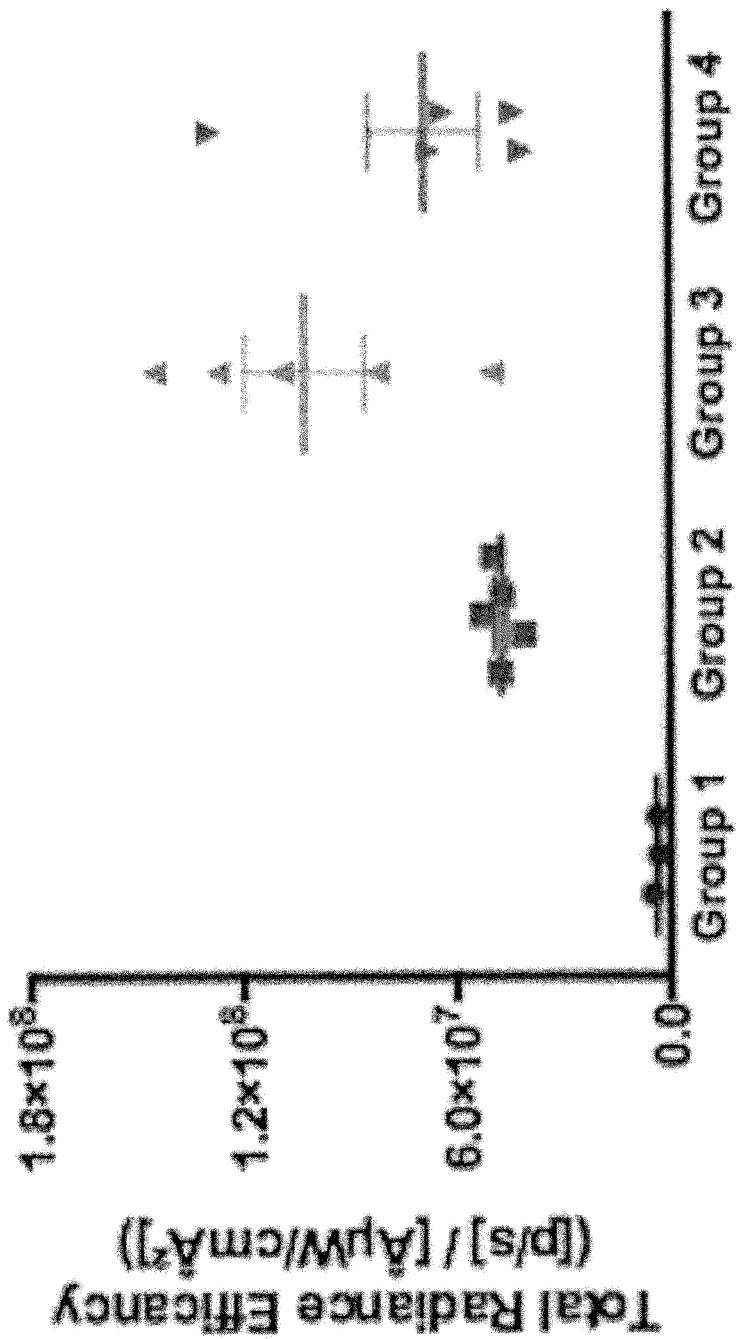
FIG. 8 Nanoparticles are localised selectively: Mean total radiant efficiency+− SEM $(p/s)/[A_\mu W/cmA^2])$ for excised tumour at 96 hr time point. Vehicle control (PBS; Group 1), uncoated nanoparticles (Group 2); Ab-coated nanoparticles (Group 3) and HEL4-coated nanoparticles (Group 4) were administered in a 50 µL volume once on Study Day 0 via intravenous tail vein injection FIG. 9 NIR signal strength at 96 hr. Ex vivo bioluminescence imaging showed antibody coated NPs had higher accumulation in the excised tumour than naked nanoparticles. A: PBS group; B: uncoated nanoparticles; C: antibody coated nanoparticles; D: HEL4-coated nanoparticles.

FIG. 8 shows that the nanoparticles are localised selectively: Mean total radiant efficiency+−SEM (p/s)/[$A_μ$W/$cmA^2$]) for excised tumour at 96 hr time point. Vehicle control (PBS; Group 1), uncoated nanoparticles (Group 2); Ab-coated nanoparticles (Group 3) and HEL4-coated nanoparticles (Group 4) were administered in a 50 μL volume once on Study Day 0 via intravenous tail vein injection.

Example 4: Efficacy of Gemcitabine Liposome Nanoparticles Conjugated to a Domain for Binding to $P2X_7R$ This study aimed to determine the efficacy of $P2X_7$-binding domain-coated nanoparticles (i.e., "BIL03s-coated") and HEL4-coated nanoparticles to deliver the cytotoxic agent gemcitabine to tumours in the 4T1 murine breast tumour model.

Nanoparticles were administered intravenously, 3 times a week. Nanoparticles contained either 0.2 mg gemcitabine or PBS buffer (control).

Figure 10:
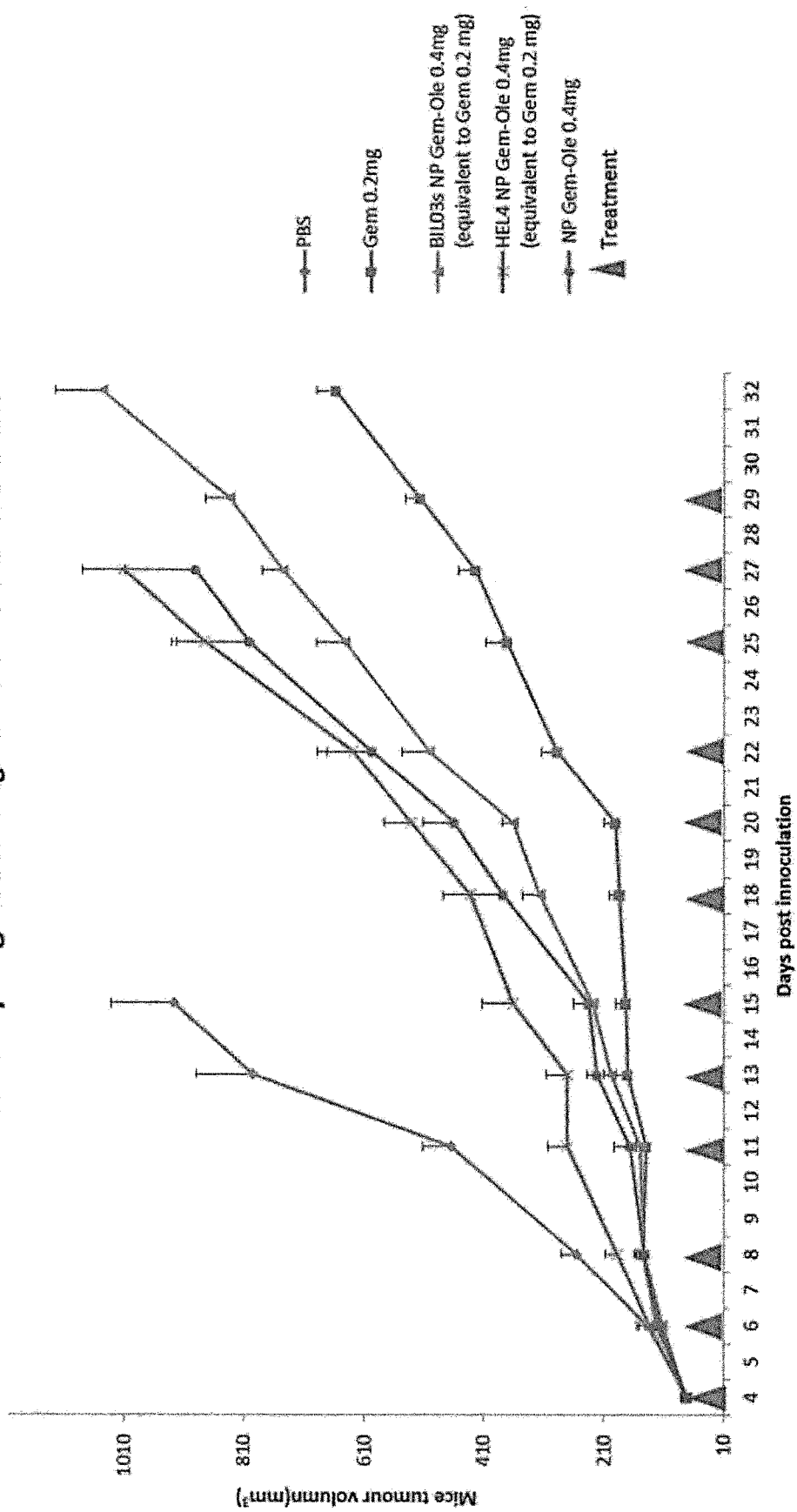
FIG. 10 Efficacy of antibody-conjugated nanoparticles on 4T1 murine breast tumour bearing mice: The mean tumour volume for each treatment group against days post inoculation. Treatment was given intravenously three times per week.
Figure 10:
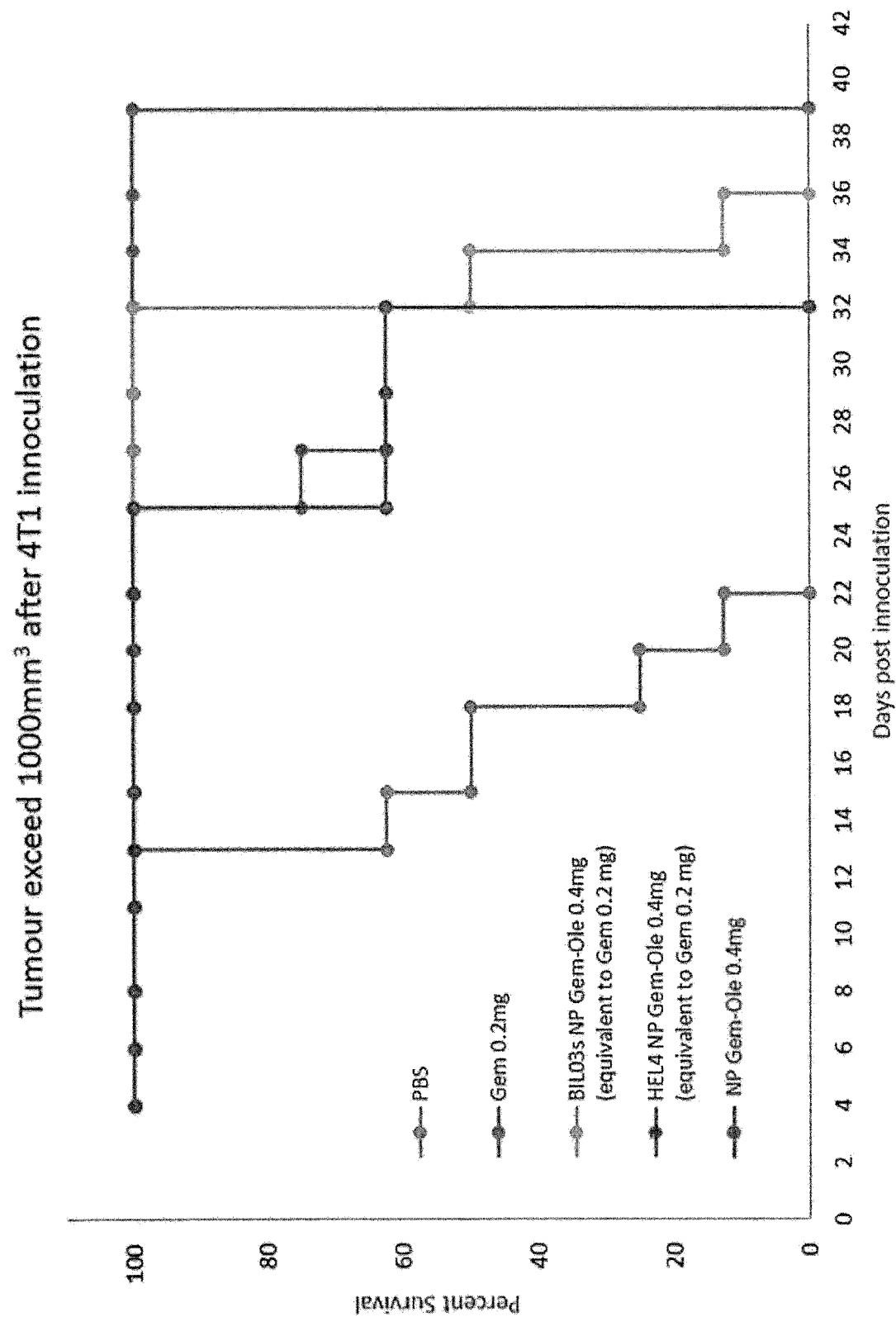

Tumour volume was measured over the study period (see FIG. 10). Mice were terminated when estimated tumour volume exceeded 1000 $mm^3$.

Figure 11:
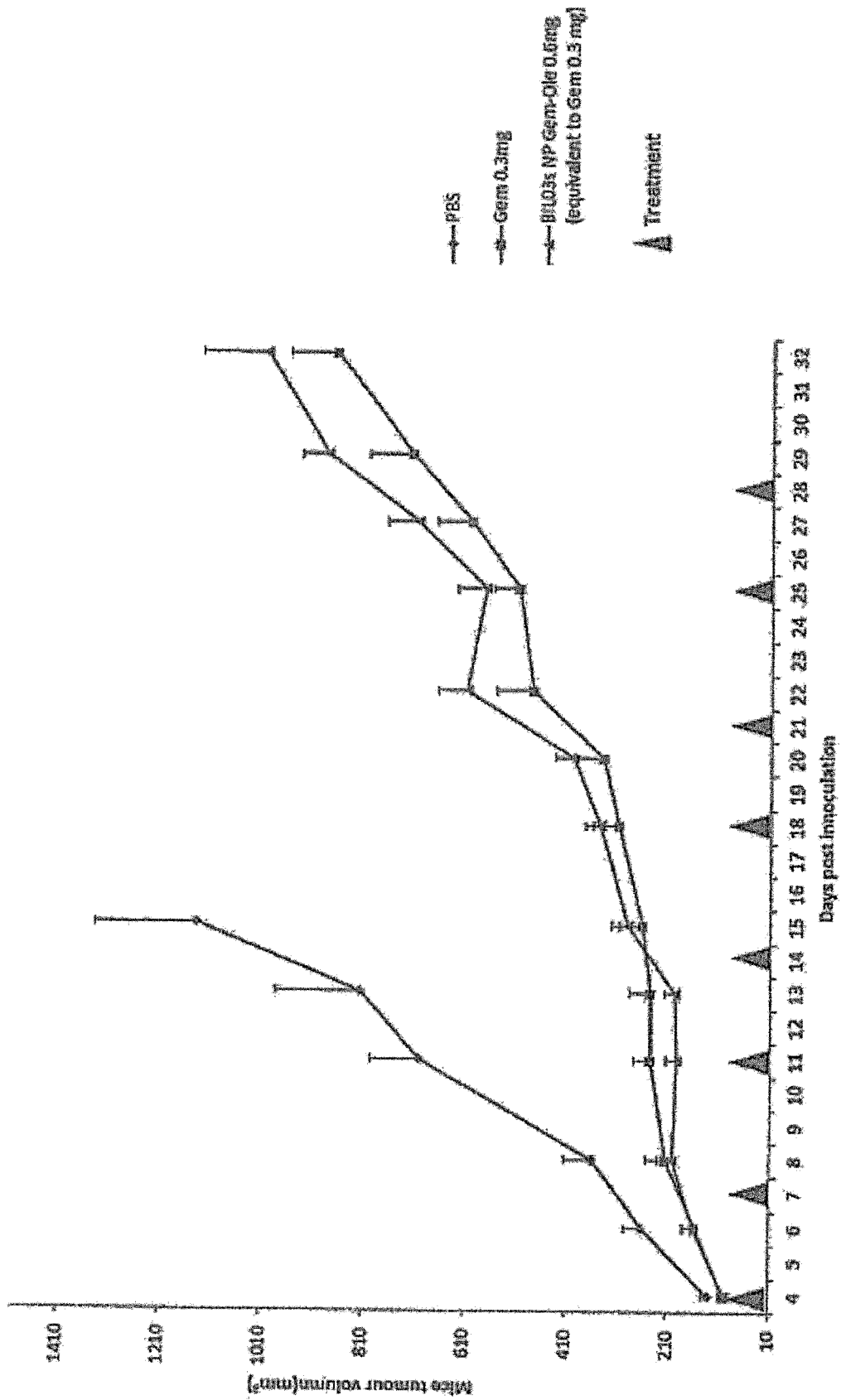
FIG. 11 The effect of dosing frequency of antibody-coated nanoparticles: The mean tumour volume for each treatment group against days post inoculation. Treatment was given intravenously twice per week.
Figure 11:
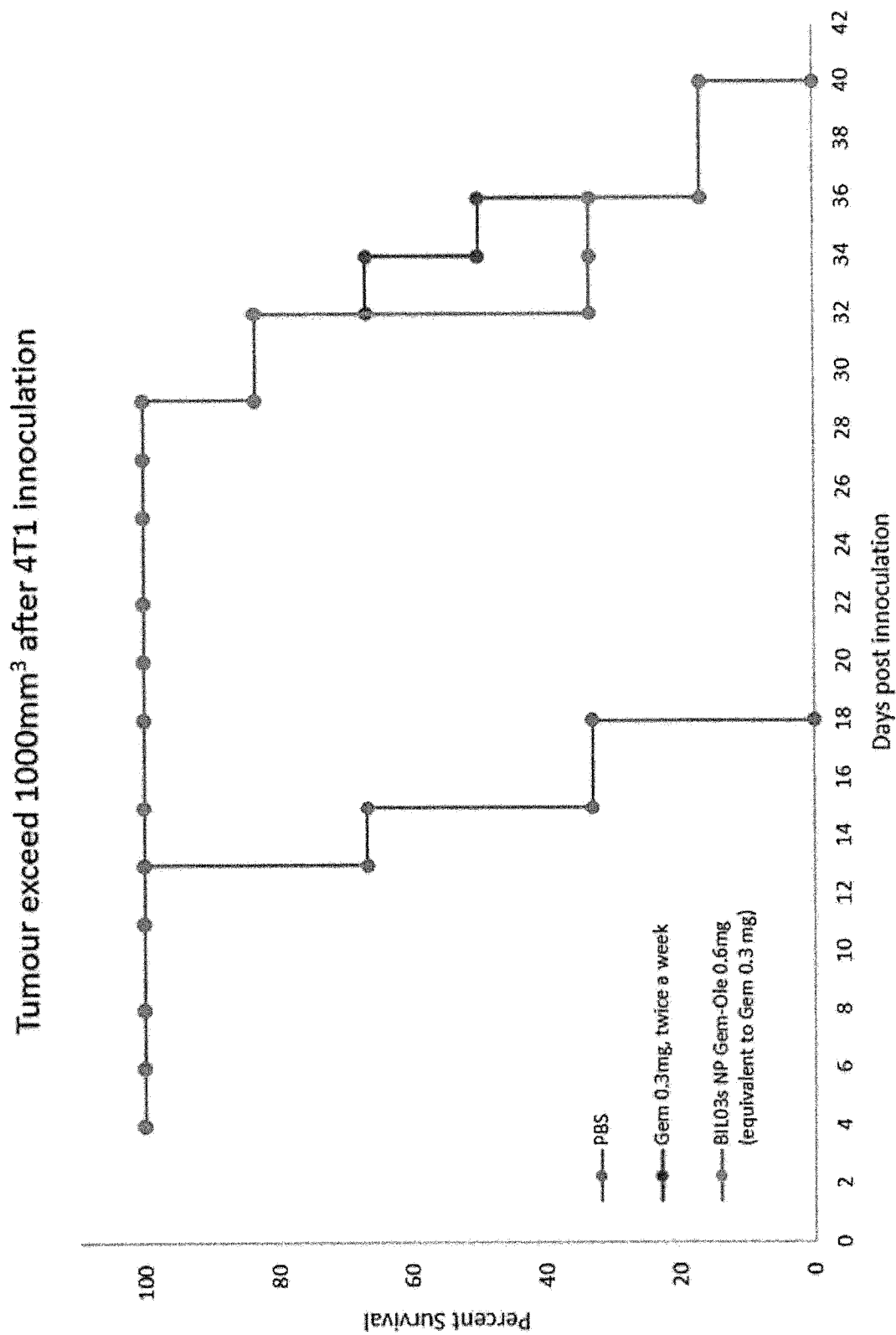

FIG. 10 shows efficacy of antibody-conjugated nanoparticles on 4T1 murine breast tumour bearing mice. FIG. 11 shows the effect of dosing frequency of antibody-coated nanoparticles.

The results showed that the $P2X_7$-binding domain-coated nanoparticles containing gemcitabine provided greater tumour suppression and prolonged survival compared with HEL4-coated nanoparticles containing gemcitabine (P=0.0456).

Example 5: Dosing Regimen Investigation

FIG. 11 shows the results of a study comparing the efficacy of $P2X_7$-binding domain-coated nanoparticles containing gemcitabine to gemcitabine alone for inhibiting tumour growth. The study compared the results following administration of 0.3 mg gemcitabine ("free gemcitabine") or $P2X_7$-binding domain-coated nanoparticles containing gemcitabine, equivalent to a dose of 0.3 mg gemcitabine.

The efficacy of both treatments was comparable, indicating that one benefit of the $P2X_7$-binding domain-coated nanoparticles is the ability to reduce the frequency of dosing if using $P2X_7$-binding domain-coated nanoparticles.

The coated nanoparticles provide for sustained release and lower toxicity, thereby providing an advantage over existing cancer treatments.

The findings of in vivo studies also indicate that greater efficacy of P2X$_7$-binding domain-coated nanoparticles containing gemcitabine over commercially available gemcitabine may be obtained by increasing the amount of gemcitabine administered while decreasing the frequency of dosing. In other words, lower treatment frequency resulted in equivalent efficacy to current gemcitabine dosing regimens.

---

The invention claimed is:

1. A cytotoxic particle including:
a liposome;
a prodrug of a cytotoxic compound contained in, or entrapped in or on a lipid bilayer of said liposome;
a plurality of variable domains arranged on the liposome for binding to P2X$_7$ Receptors (P2X$_7$R) on a cancer cell thereby enabling the particle to bind to a cancer cell having P2X$_7$R expressed thereon when the particle is contacted with the cancer cell,
wherein the variable domains are selected from the group consisting of: a single domain antibody (sdAb), a single chain Fv fragment (scFv), F(ab')2, Fab, Fd and Fv fragments;
wherein the variable domains bind to cancer-associated P2X-R that have an impaired response to ATP such that they are unable to form an apoptotic pore under normal physiological conditions and wherein the variable domains do not bind P2X-R that do not have an impaired response to ATP.

2. The particle of claim 1 wherein the cytotoxic compound is gemcitabine.

3. The particle of claim 2 wherein the liposome includes hydrocarbon chains forming a lipid layer of the liposome and wherein the primary amine of gemcitabine is bonded to a hydrocarbon chain of the lipid layer via a carbamate group.

4. The particle of claim 2 wherein the liposome includes maleimide groups arranged thereon enabling conjugation of an antibody to the liposome.

5. The particle of claim 1, wherein the variable domain binds to a peptide consisting of the sequence GHNYTTNILPGLNITC (SEQ ID NO: 2).

6. The particle of claim 1, wherein the variable domain binds to a peptide consisting of the sequence KYYKENNVEKRTLIK (SEQ ID NO: 3).

7. The particle of claim 1 wherein the variable domain is defined by Formula 1:

CDR1-CDR2-CDR3 wherein CDR1 is RNHDMG (SEQ ID NO: 4)
   wherein CDR2 is AISGSGGSTYYANSVKG (SEQ ID NO: 5)
   wherein CDR3 is EPKPMDTEFDY (SEQ ID NO: 6).

8. The particle of claim 1 wherein the variable domain comprises the amino acid sequence as shown in SEQ ID NO: 7.

9. The particle of claim 1 wherein the variable domain consisting of the amino acid sequence as shown in SEQ ID NO: 7.

10. The particle of claim 1, wherein the variable domain comprises or consists of the amino acid sequence as shown in SEQ ID NO: 8.

11. A pharmaceutical composition including a plurality of cytotoxic particles and a pharmaceutically effective diluent, excipient or carrier, wherein the cytotoxic particles include:
a liposome;
a prodrug of a cytotoxic compound contained in or on a lipid bilayer of said liposome;
a plurality of variable domains arranged on the core for binding to P2X$_7$R on a cancer cell thereby enabling the particle to bind to a cancer cell having P2X$_7$R expressed thereon when the particle is in contact with the cancer cell;
wherein the variable domains are selected from the group consisting of: a single domain antibody (sdAb), a single chain Fv fragment (scFv), F(ab')2, Fab, Fd and Fv fragments;
wherein the variable domains bind to cancer-associated P2X$_7$R that have an impaired response to ATP such that they are unable to form an apoptotic pore under normal physiological conditions and wherein the variable domains do not bind P2X$_7$R that do not have an impaired response to ATP.

12. The pharmaceutical composition of claim 11 wherein the variable domain of the cytotoxic particle binds to a peptide consisting of the sequence GHNYTTNILPGLNITC (SEQ ID NO: 2).

13. The pharmaceutical composition of claim 11, wherein the variable domain of the cytotoxic particle binds to a peptide consisting of the sequence KYYKENNVEKRTLIK (SEQ ID NO: 3).

14. The pharmaceutical composition of claim 11, wherein the variable domain of the cytotoxic particle is defined by Formula 1: CDR1-CDR2-CDR3
   wherein CDR1 is RNHDMG (SEQ ID NO: 4)
   wherein CDR2 is AISGSGGSTYYANSVKG (SEQ ID NO: 5)
   wherein CDR3 is EPKPMDTEFDY (SEQ ID NO: 6).

15. The pharmaceutical composition of claim 11 wherein the variable domain comprises or consists of the amino acid sequence as shown in SEQ ID NO: 7.

16. A method of treating an individual having cancer including administering a particle of claim 1 to the individual, thereby treating the individual for cancer.

17. The method of claim 16, wherein the cancer is a solid tumour.

18. The method of claim 17, wherein the cancer is breast cancer.

19. A method for killing a cancer cell including contacting a cancer cell with a particle of claim 1.

* * * * *

UNITED STATES PATENT AND TRADEMARK OFFICE
CERTIFICATE OF CORRECTION

PATENT NO. : 12,097,265 B2  
APPLICATION NO. : 17/575568  
DATED : September 24, 2024  
INVENTOR(S) : Xiaojuan Gong et al.

Page 1 of 1

It is certified that error appears in the above-identified patent and that said Letters Patent is hereby corrected as shown below:

In the Specification

In Column 14, Line 2, delete "unilameilar" and replace it with --unilamellar--.

In the Claims

In Column 27, Claim 1, Lines 33 and 36, delete "P2X-R" and replace it with --P2X7R--.

Signed and Sealed this  
Thirty-first Day of December, 2024

Derrick Brent  
*Acting Director of the United States Patent and Trademark Office*